US009993405B2

(12) United States Patent
Roudot et al.

(10) Patent No.: US 9,993,405 B2
(45) Date of Patent: *Jun. 12, 2018

(54) COSMETIC OR DERMATOLOGICAL COMPOSITION COMPRISING A MEROCYANINE AND AN OILY PHASE COMPRISING AT LEAST ONE SPECIFIC AMIDE COMPOUND

(71) Applicant: L'OREAL, Paris (FR)

(72) Inventors: Angelina Roudot, Le Kremlin Bicêtre (FR); Didier Candau, Bievres (FR); Xavier Marat, Paris (FR); Alexandre Cavezza, Les Pavillons sous Bois (FR)

(73) Assignee: L'OREAL, Paris (FR)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/762,052

(22) PCT Filed: Jan. 20, 2014

(86) PCT No.: PCT/EP2014/051018
§ 371 (c)(1),
(2) Date: Jul. 20, 2015

(87) PCT Pub. No.: WO2014/111570
PCT Pub. Date: Jul. 24, 2014

(65) Prior Publication Data
US 2015/0359718 A1    Dec. 17, 2015

(30) Foreign Application Priority Data

Jan. 21, 2013 (FR) .................................... 13 50486

(51) Int. Cl.
| | | |
|---|---|---|
| A61Q 17/04 | (2006.01) | |
| A61Q 19/00 | (2006.01) | |
| A61Q 19/04 | (2006.01) | |
| A61Q 19/08 | (2006.01) | |
| A61K 8/42 | (2006.01) | |
| A61K 8/41 | (2006.01) | |
| A61K 8/06 | (2006.01) | |

(52) U.S. Cl.
CPC ............... *A61K 8/42* (2013.01); *A61K 8/062* (2013.01); *A61K 8/41* (2013.01); *A61Q 17/04* (2013.01); *A61Q 19/00* (2013.01); *A61Q 19/004* (2013.01); *A61Q 19/08* (2013.01); *A61K 2800/592* (2013.01)

(58) Field of Classification Search
None
See application file for complete search history.

(56) References Cited

U.S. PATENT DOCUMENTS

| 4,085,217 A * | 4/1978 | Kalopissis | A61K 8/447 424/70.8 |
| 2013/0064871 A1* | 3/2013 | Richard | A61K 8/35 424/401 |
| 2014/0294743 A1* | 10/2014 | Richard | A61K 8/41 424/59 |

FOREIGN PATENT DOCUMENTS

WO    WO 2008080892 A1 *   7/2008

* cited by examiner

Primary Examiner — Jyothsna A Venkat
(74) Attorney, Agent, or Firm — Polsinelli PC

(57) ABSTRACT

The present invention relates to a cosmetic or dermatological composition comprising, in a physiologically acceptable support: a) at least one merocyanine of formula (1) or (2). b) at least one oily phase comprising at least one amide compound of formula (I). The present invention also relates to a non-therapeutic cosmetic process for caring for and/or making up a keratin material, comprising the application, to the surface of the said keratin material, of at least one composition as defined above. The invention also relates to a non-therapeutic cosmetic process for limiting the darkening of the skin and/or improving the color and/or uniformity of the complexion, comprising the application, to the surface of the keratin material, of at least one composition as defined previously. The invention also relates to a non-therapeutic cosmetic process for preventing and/or treating the signs of ageing of a keratin material, comprising the application, to the surface of the keratin material, of at least one composition as defined previously.

2 Claims, No Drawings

COSMETIC OR DERMATOLOGICAL COMPOSITION COMPRISING A MEROCYANINE AND AN OILY PHASE COMPRISING AT LEAST ONE SPECIFIC AMIDE COMPOUND

CROSS REFERENCE TO RELATED APPLICATIONS

This application is a National Phase filing under 35 U.S.C. § 371 of PCT/EP2014/051018 filed on Jan. 20, 2014; and this application claims priority to Application No. 1350486 filed in France on Jan. 21, 2013. The entire contents of each application are hereby incorporated by reference.

The present invention relates to a cosmetic or dermatological composition comprising, in a physiologically acceptable support:
a) at least one merocyanine of formula (1) or (2) which will be defined in detail hereinbelow and
b) at least one oily phase comprising at least one amide compound of formula (I) which will be defined in detail hereinbelow.

The present invention also relates to a non-therapeutic cosmetic process for caring for and/or making up a keratin material, comprising the application, to the surface of the said keratin material, of at least one composition according to the invention as defined above.

The invention also relates to a non-therapeutic cosmetic process for limiting the darkening of the skin and/or improving the colour and/or uniformity of the complexion, comprising the application, to the surface of the keratin material, of at least one composition as defined previously.

The invention also relates to a non-therapeutic cosmetic process for preventing and/or treating the signs of ageing of a keratin material, comprising the application, to the surface of the keratin material, of at least one composition as defined previously.

It is known that radiation with wavelengths of between 280 nm and 400 nm permits tanning of the human epidermis and that radiation with wavelengths of between 280 and 320 nm, known as UV-B rays, harms the development of a natural tan. Exposure is also liable to bring about a detrimental change in the biomechanical properties of the epidermis, which is reflected by the appearance of wrinkles, leading to premature ageing of the skin.

It is also known that UV-A rays with wavelengths of between 320 and 400 nm penetrate more deeply into the skin than UV-B rays. UV-A rays cause immediate and persistent browning of the skin. Daily exposure to UVA rays, even of short duration, under normal conditions can result in damage to the collagen fibres and the elastin, which is reflected by a modification in the microrelief of the skin, the appearance of wrinkles and uneven pigmentation (liver spots, lack of uniformity of the complexion).

Protection against UVA and UVB rays is thus necessary. An efficient photoprotective product should protect against both UVA and UVB radiation.

Many photoprotective compositions have been proposed to date to overcome the effects induced by UVA and/or UVB radiation. They generally contain organic or mineral UV-screening agents, which function according to their own chemical nature and according to their own properties by absorption, reflection or scattering of the UV radiation. They generally comprise mixtures of liposoluble organic screening agents and/or water-soluble UV screening agents in combination with metal oxide pigments, such as titanium dioxide or zinc oxide.

Many cosmetic compositions for limiting the darkening of the skin and improving the colour and uniformity of the complexion have been proposed to date. It is well known in the field of antisun products that such compositions may be obtained by using UV-screening agents, and in particular UVB-screening agents. Certain compositions may also contain UVA-screening agents. This screening system should cover UVB protection for the purpose of limiting and controlling the neosynthesis of melanin, which promotes the overall pigmentation, but should also cover UVA protection so as to limit and control the oxidation of the already-existing melanin leading to darkening of the skin colour.

However, it is extremely difficult to find a composition which contains a particular combination of UV-screening agents that would be especially suited to photoprotecting the skin and particularly to improving the quality of the skin as regards both the colour and its mechanical elasticity properties.

Advantageously, this improvement is particularly sought on already-pigmented skin so as not to increase the melanin pigmentary load or the structure of the melanin already present in the skin.

In point of fact, the majority of the organic UV-screening agents consist of aromatic compounds which absorb in the wavelength range between 280 and 370 nm. In addition to their power for screening out sunlight, the desired photoprotective compounds should also have good cosmetic properties, good solubility in the usual solvents and in particular in fatty substances such as oils, and also good chemical stability and good photostability alone or in combination with other UV-screening agents. They should also be colourless or at least have a colour that is cosmetically acceptable to the consumer.

One of the main drawbacks known to date of these compositions is that these screening systems are insufficiently effective against UV rays and in particular against long UVA rays with wavelengths beyond 370 nm, for the purpose of controlling photo-induced pigmentation and its evolution by means of a system for screening out UV over the entire UV spectrum.

Among all the compounds that have been recommended for this purpose an advantageous family of UV-screening agents has been proposed, which consists of carbon-bearing merocyanine derivatives, which is described in U.S. Pat. No. 4,195,999, patent application WO 2004/006 878, patent applications WO2008/090066, WO2011/113718, WO2009/027258, WO2013/010590, WO2013/011094, WO2013/011480 and the documents IP COM JOURNAL No. 000179675D published on Feb. 23, 2009, IP COM JOURNAL No. 000182396D published on April 29, IP COM JOURNAL No. 000189542D published on Nov. 12, 2009, IP COM Journal No. IPCOM000011179D published on Mar. 4, 2004. Some of these compounds may show the following drawbacks:
  relatively unsatisfactory solubility in the usual solvents and in particular in fatty substances such as oils which may require a laborious formulation process and/or may result in cosmetic drawbacks such as a greasy effect on application;
  an unsatisfactory chemical stability and/or unsatisfactory photostability
  produce a color liable to discourage the consumer from using a cosmetic or dermatological composition containing them.

There is thus still a need to find new formulations comprising an oily phase and at least one merocyanine compound without the drawbacks as previously defined.

The Applicant has discovered, surprisingly, that this objective could be reached with a cosmetic or dermatological composition comprising, in a physiologically acceptable support:

a) at least one merocyanine of formula (1) or (2) which will be defined in detail hereinbelow and b) at least one oily phase comprising at least one amide compound of formula (I) which will be defined in detail herein below.

Furthermore, the merocyanine compounds of formula (1) or (2) herein below, present surprisingly the advantage to be significantly less colored than the merocyanine compounds as disclosed in the application WO2008/090066 as the compound MC11 also called MC03 in the application WO2009/027258.

Those discoveries form the basis of the present invention.

Thus, in accordance with one of the objects of the present invention, a cosmetic or dermatological composition is now proposed, comprising, in a physiologically acceptable support:

c) at least one merocyanine of formula (1) or (2) which will be defined in detail herein below and d) at least one oily phase comprising at least one amide compound of formula (I) which will be defined in detail hereinbelow.

The present invention also relates to a non-therapeutic cosmetic process for caring for and/or making up a keratin material, comprising the application, to the surface of the said keratin material, of at least one composition according to the invention as defined above.

The invention also relates to a non-therapeutic cosmetic process for limiting the darkening of the skin and/or improving the colour and/or uniformity of the complexion, comprising the application, to the surface of the keratin material, of at least one composition as defined previously.

The invention also relates to a non-therapeutic cosmetic process for preventing and/or treating the signs of ageing of a keratin material, comprising the application, to the surface of the keratin material, of at least one composition as defined previously.

Other characteristics, aspects and advantages of the invention will emerge on reading the detailed description that follows.

The expression "human keratin materials" means the skin (body, face, area around the eyes), hair, eyelashes, eyebrows, body hair, nails, lips or mucous membranes.

The term "physiologically acceptable" means compatible with the skin and/or its integuments, having a pleasant colour, odour and feel and not causing any unacceptable discomfort (stinging, tautness or redness) liable to discourage the consumer from using this composition.

The term "between X and Y" means the range of values also including the limits X and Y.

According to the invention, the term "preventing" or "prevention" means reducing the risk of occurrence or slowing down the occurrence of a given phenomenon, namely, according to the present invention, the signs of ageing of a keratin material.

Merocyanines

According to the present invention, the merocyanine compounds in accordance with the invention correspond to formula (1) or (2) below

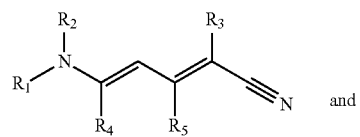

and

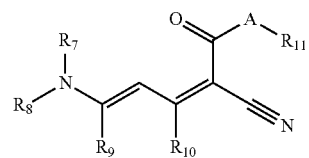

in which:

$R_1$ and $R_2$ are, independently of each other, hydrogen; a $C_1$-$C_{22}$ alkyl group, a $C_2$-$C_{22}$ alkenyl group or a $C_2$-$C_{22}$ alkynyl group, it being possible for these groups to be substituted with at least one hydroxyl group or to be interrupted with at least one —O—; or alternatively $R_1$ and $R_2$ form, together with the nitrogen atom which connects them, a —$(CH_2)_n$— ring which may optionally be interrupted with —O— or —NH—;

$R_3$ is a group —(C=O)$OR_6$ or a group —(CO)$NHR_6$;

$R_6$ is a $C_1$-$C_{22}$ alkyl group, a $C_2$-$C_{22}$ alkenyl group, a $C_2$-$C_{22}$ alkynyl group, a $C_3$-$C_{22}$ cycloalkyl group or a $C_3$-$C_{22}$ cycloalkenyl group, it being possible for the said groups to be substituted with one or more OH groups;

$R_4$ and $R_5$ are hydrogens; or $R_4$ and $R_5$ form a —$(CH_2)_n$— ring which may be substituted with a $C_1$-$C_4$ alkyl group and/or interrupted with one or more —O— or with —NH—;

n is a number between 2 and 7;

$R_7$ and $R_8$ are, independently of each other, hydrogen; a $C_1$-$C_{22}$ alkyl group, a $C_2$-$C_{22}$ alkenyl group or a $C_2$-$C_{22}$ alkynyl group, it being possible for the said groups to be interrupted with one or more O and/or substituted with one or more OH groups; a $C_3$-$C_{22}$ cycloalkyl group or a $C_3$-$C_{22}$ cycloalkenyl group, it being possible for the said groups to be interrupted with one or more —O—;

or alternatively $R_7$ and $R_8$ form, together with the nitrogen which connects them, a —$(CH_2)_n$— ring which may be interrupted with one or more —O—;

$R_9$ and $R_{10}$ are hydrogen; or $R_9$ and $R_{10}$ form a —$(CH_2)_n$— ring which may be substituted with a $C_1$-$C_4$ alkyl and/or interrupted with an —O— or —NH—;

A is —O— or —NH;

$R_{11}$ is a $C_1$-$C_{22}$ alkyl group; a $C_2$-$C_{22}$ alkenyl group; a $C_2$-$C_{22}$ alkynyl group; a $C_3$-$C_{22}$ cycloalkyl group or a $C_3$-$C_{22}$ cycloalkenyl group, it being possible for the said groups to be interrupted with one or more O; or a $C_1$-$C_{22}$ alkyl group or a $C_2$-$C_{22}$ alkenyl group which is substituted with a $C_3$-$C_{22}$ cycloalkyl group or a $C_3$-$C_{22}$ cycloalkenyl group, it being possible for the said $C_3$-$C_{22}$ cycloalkyl group or $C_3$-$C_{22}$ cycloalkenyl group to be interrupted with one or more —O—;

with the proviso that:

(I) at least one of the groups $R_1$, $R_2$ or $R_6$ is substituted with a hydroxyl;

(II) if one of the groups $R_1$ denotes a hydroxyethyl, $R_2$ does not denote a hydrogen, a methyl or an ethyl, or a hydroxyethyl; and if $R_1$ denotes hydrogen, $R_2$ is not 1-hydroxy-3-methyl-2-butyl;

(III) if $R_6$ is substituted with one or more OH groups, one from among $R_1$ and $R_2$ is a $C_4$-$C_{22}$ alkyl group; or alternatively $R_1$ and $R_2$ form, together with the nitrogen to which they are attached, a piperidyl or morpholinyl radical;

(IV) at least one among the radicals $R_7$, $R_8$ and $R_{11}$ is interrupted with one or more —O—.

The preferred compounds are those of formula (1) or (2) in which:

$R_1$ and $R_2$ are, independently of each other, hydrogen; a $C_4$-$C_{12}$ alkyl group; or a $C_3$-$C_{12}$ hydroxyalkyl group; or at least one from among $R_1$ and $R_2$ is a $C_3$-$C_{12}$ hydroxyalkyl; and $R_3$, $R_4$ and $R_5$ have the same meanings as previously.

The preferred compounds are also those of formula (1) in which:

$R_6$ is a $C_1$-$C_{12}$ alkyl group which may be substituted with one or more hydroxyls.

The most preferential compounds are also those of formula (1) in which:

$R_6$ is a $C_1$-$C_{12}$ alkyl group which may be substituted with one or more hydroxyls;

one of the radicals $R_1$ or $R_2$ is a $C_4$-$C_{22}$ alkyl group; or alternatively $R_1$ and $R_2$ form, together with the nitrogen which connects them, a —$(CH_2)_n$— ring which may be interrupted with —O— and/or —NH—; and $R_4$ and $R_5$ and n have the same meanings indicated previously.

The preferred compounds are those of formula (2) in which:

$R_{11}$ is a radical —$(CH_2)_m$—O—$R_{12}$, in which $R_{12}$ is a $C_1$-$C_{12}$ alkyl group or a $C_1$-$C_6$-alkoxy-$C_1$-$C_6$-alkyl group;

m is a number from 1 to 5; and $R_7$, $R_8$, $R_9$, $R_{10}$ and A have the same meanings indicated previously.

The even more preferential compounds are those of formula (1) or (2) in which:

$R_1$ and $R_2$, on the one hand, and $R_7$ and $R_8$, on the other hand, respectively form, together with the nitrogen atom to which they are respectively attached, a piperidyl radical or a morpholinyl radical.

The preferred compounds are also those of formula (1) or (2) in which:

$R_4$ and $R_5$ and $R_9$ and $R_{10}$ respectively form a carbon-based ring which contains 6 carbon atoms.

The most preferential compounds are those of formula (1) in which:

$R_1$ and $R_2$ are, independently of each other, a hydrogen; or a $C_1$-$C_{22}$ alkyl group; or a $C_1$-$C_{22}$ hydroxyalkyl group; or $R_1$ and $R_2$ form, together with the nitrogen to which they are attached, a piperidyl or morpholinyl radical;

$R_3$ is a group —(C=O)$OR_6$ or a group —(CO)$NHR_6$;

$R_6$ is a $C_1$-$C_{22}$ alkyl group which may be substituted with one or more —OH;

$R_4$ and $R_5$ are a hydrogen; or $R_4$ and $R_5$ are linked together to form a carbon-based ring which contains 6 carbon atoms.

The most preferential compounds are those of formula (1) in which:

$R_1$ and $R_2$ are, independently of each other, a hydrogen; or a $C_1$-$C_{22}$ hydroxyalkyl group; in which at least one of the radicals $R_1$ and $R_2$ is a $C_1$-$C_{22}$ hydroxyalkyl group;

$R_3$ is a group —(C=O)$OR_6$ or a group —(C=O)$NHR_6$;

$R_6$ is a $C_1$-$C_{22}$ alkyl group; and $R_4$ and $R_5$ are hydrogens; or $R_4$ and $R_5$ are linked together to form a carbon-based ring which contains 6 carbon atoms.

The most preferential compounds are those of formula (2) in which:

$R_7$ and $R_8$ are, independently of each other, a hydrogen or a $C_1$-$C_8$ alkyl group which may be interrupted with one or more —O—;

A is —O— or —NH;

$R_{11}$ is a $C_1$-$C_{22}$ alkyl; and $R_9$ and $R_{10}$ are a hydrogen; or $R_9$ and $R_{10}$ are linked together to form a carbon-based ring which contains 6 carbon atoms.

The most preferential compounds are those of formula (2) in which:

$R_7$ and $R_8$ form, together with the nitrogen atom to which they are bonded, a morpholinyl or piperidyl radical;

A is —O— or —NH;

$R_{11}$ is a $C_1$-$C_{22}$ alkyl group which may be interrupted with one or more —O—; and $R_9$ and $R_{10}$ are hydrogens; or $R_9$ and $R_{10}$ are linked together to form a carbon-based ring which contains 6 carbon atoms.

The even more preferential compounds are those of formula (2) in which:

$R_{11}$ is a radical —$(CH_2)_m$—O—$R_{12}$, in which $R_{12}$ is a $C_1$-$C_4$ alkyl group or a $C_1$-$C_4$-alkoxy-$C_1$-$C_4$-alkyl group;

m is a number from 1 to 3;

$R_7$ and $R_8$ are, independently of each other, a hydrogen; a $C_1$-$C_{12}$ alkyl group which may be interrupted with one or more O; or $R_7$ and $R_8$ form, together with the nitrogen atom to which they are attached, a morpholinyl or piperidyl radical;

$R_9$ and $R_{10}$ are hydrogens or together form a carbon-based ring which contains 6 carbon atoms; and A is —O— or —NH.

The merocyanine compounds of the invention may be in the E/E-, E/Z- or Z/Z geometrical isomer form.

The alkyl, cycloalkyl, alkenyl, alkylidene or cycloalkenyl chains may be linear or branched, monocyclic or polycyclic chains.

A $C_1$-$C_{22}$ alkyl group is, for example, a methyl, ethyl, n-propyl, isopropyl, n-butyl, sec-butyl, isobutyl, tert-butyl, n-pentyl, 2-pentyl, 3-pentyl, 2,2-dimethylpropyl, n-hexyl, n-octyl, 1,1,3,3-tetramethylbutyl, 2-ethylhexyl, nonyl, decyl, n-octadecyl, eicosyl or dodecyl.

A substituted alkyl group is, for example, a methoxyethyl, ethoxypropyl, 2-ethylhexyl, hydroxyethyl, chloropropyl, N,N-diethylaminopropyl, cyanoethyl, phenethyl, benzyl, p-tert-butylphenethyl, p-tert-octylphenoxyethyl, 3-(2,4-di-tert-amylphenoxy)propyl, ethoxycarbonylmethyl-2-(2-hydroxyethoxyl)ethyl or 2-furylethyl.

A hydroxyalkyl group is, for example, a hydroxymethyl, hydroxyethyl, hydroxypropyl, hydroxybutyl, hydroxypentyl, hydroxyhexyl, hydroxyheptyl, hydroxyoctyl, hydroxynonyl or hydroxydecyl.

A $C_2$-$C_{22}$ alkenyl group is, for example, a linear $C_2$-$C_{12}$ alkenyl chain or, preferentially, a branched $C_3$-$C_{12}$ alkenyl. A $C_2$-$C_{22}$ alkenyl is, for example, a vinyl, allyl, 2-propen-2-yl, 2-buten-1-yl, 3-butane-1-yl, 1,3-butadien-2-yl, 2-cyclobuten-1-yl, 2-penten-1-yl, 3-penten-2-yl, 2-methyl-1-buten-3-yl, 2-methyl-3-buten-2-yl, 3-methyl-2-buten-1-yl, 1,4-pentadien-3-yl, 2-cyclopenten-1-yl, 2-cyclohexen-1-yl, 3-cyclohexen-1-yl, 2,4-cyclohexadien-1-yl, 1-p-menthen-8-yl, 4(10)-thujen-10-yl, 2-norbornen-1-yl, 2,5-norbornadien-1-yl, 7,7-dimethyl-2,4-norcaradien-3-yl or the various isomers of hexenyl, octenyl, nonenyl, decenyl or dodecenyl.

A $C_3$-$C_{12}$ cycloalkyl group is, for example, a cyclopropyl, cyclobutyl, cyclopentyl, trimethylcyclohexyl or, preferentially, cyclohexyl.

Examples of merocyanines according to the present invention are listed in Table A:

TABLE A

| Compound | Structure |
| --- | --- |
| 1 | 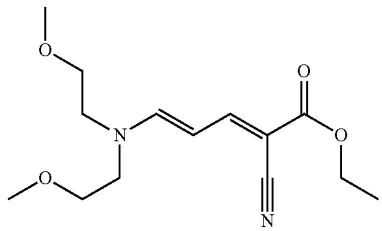 [SMILES: CCOC(=O)/C(C#N)=C/C=C/N(CCOC)CCOC] |
| 2 | 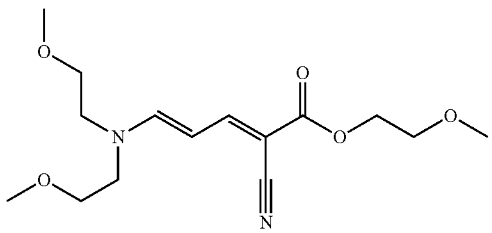 |
| 3 | 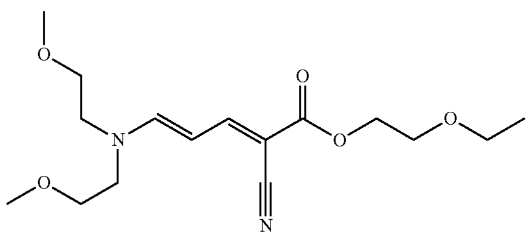 [SMILES: CCOCCOC(=O)/C(C#N)=C/C=C/N(CCOC)CCOC] |
| 4 | 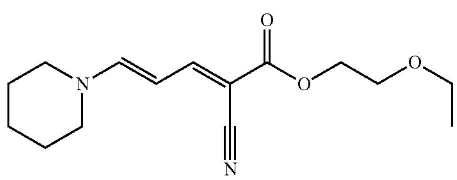 [SMILES: CCOCCOC(=O)/C(C#N)=C/C=C/N1CCCCC1] |
| 5 | 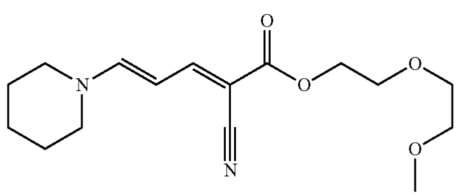 [SMILES: COCCOCCOC(=O)/C(C#N)=C/C=C/N1CCCCC1] |
| 6 | 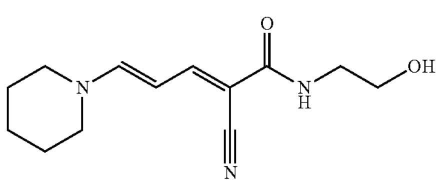 [SMILES: N#C/C(=C\C=C\N1CCCCC1)C(=O)NCCO] |
| 7 | 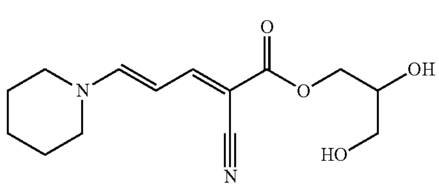 [SMILES: N#C/C(=C\C=C\N1CCCCC1)C(=O)OCC(O)CO] |

TABLE A-continued

| Compound | Structure |
| --- | --- |
| 8 | (piperidinyl-CH=CH-CH=C(CN)-C(O)-O-CH2-CH(OH)-CH2-CH2-CH3) |
| 9 | (morpholinyl-CH=CH-CH=C(CN)-C(O)-O-CH2-CH(OH)-CH2-OH) |
| 10 | (morpholinyl-CH=CH-CH=C(CN)-C(O)-O-CH2-CH2-O-CH2-CH3) |
| 11 | (dibutylamino-CH=CH-CH=C(CN)-C(O)-O-CH2-CH(OH)-CH2-OH) |
| 12 | (N(CH2CH2OH)(butyl)-CH=CH-CH=C(CN)-C(O)-O-butyl) |
| 13 | (N(CH2CH(OH)CH3)2-CH=CH-CH=C(CN)-C(O)-O-hexyl) |
| 14 | (methoxypropyl-NH-cyclohexenyl=C(CN)-C(O)-O-ethyl) |

TABLE A-continued

| Compound | Structure |
|---|---|
| 15 | 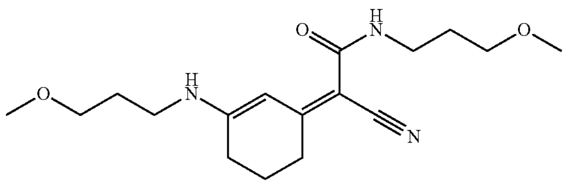 |
| 16 | 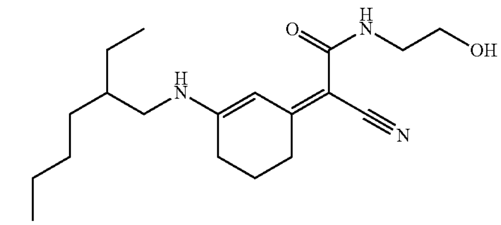 [SMILES: CCCCC(CC)CNC1=C/C(=C(/C#N)C(=O)NCCO)CCC1] |
| 17 | 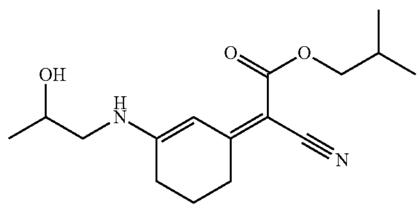 [SMILES: CC(C)COC(=O)/C(C#N)=C1\C=C(NCC(C)O)CCC1] |
| 18 | 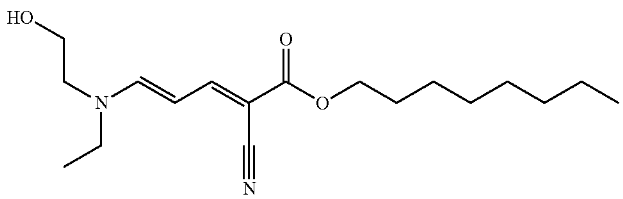 [SMILES: CCCCCCCCOC(=O)/C(C#N)=C/C=C/N(CC)CCO] |
| 19 | 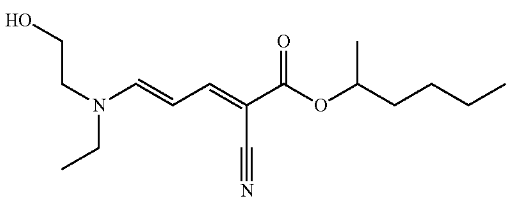 [SMILES: CCCCC(C)OC(=O)/C(C#N)=C/C=C/N(CC)CCO] |
| 20 | 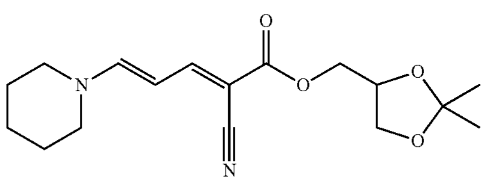 [SMILES: CC1(C)OCC(COC(=O)/C(C#N)=C/C=C/N2CCCCC2)O1] |
| 21 | 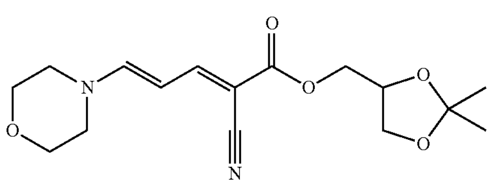 [SMILES: CC1(C)OCC(COC(=O)/C(C#N)=C/C=C/N2CCOCC2)O1] |
| 22 | 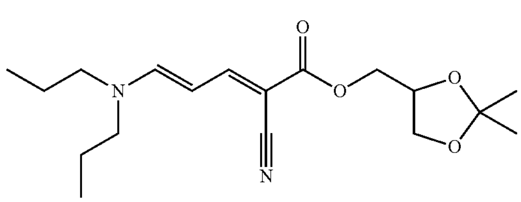 [SMILES: CCCN(/C=C/C=C(\C#N)C(=O)OCC1COC(C)(C)O1)CCC] |

TABLE A-continued

| Compound | Structure |
|---|---|
| 23 | 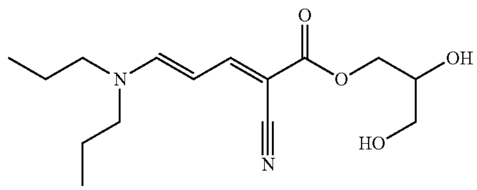 [SMILES: CCCN(/C=C/C=C(\C#N)C(=O)OCC(O)CO)CCC] |
| 24 | 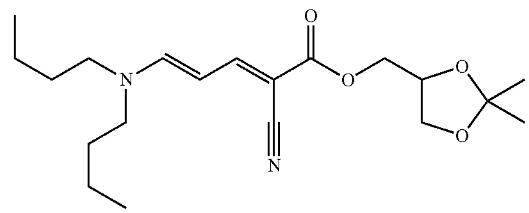 [SMILES: CCCCN(/C=C/C=C(\C#N)C(=O)OCC1COC(C)(C)O1)CCCC] |
| 25 | 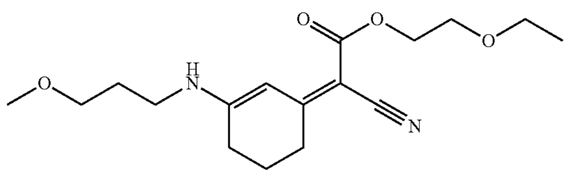 [SMILES: CCOCCOC(=O)/C(C#N)=C1\C=C(NCCCOC)CCC1] |
| 26 | 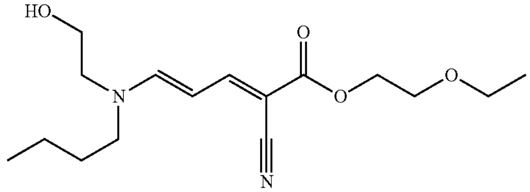 [SMILES: CCCCN(/C=C/C=C(\C#N)C(=O)OCCOCC)CCO] |
| 27 | 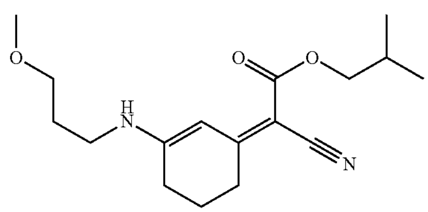 [SMILES: COCCCNC1=C/C(=C(/C#N)C(=O)OCC(C)C)CCC1] |
| 28 | 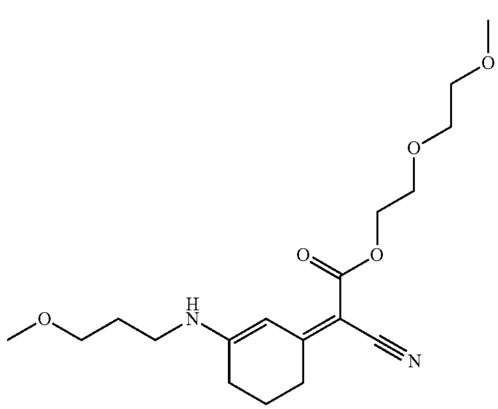 |

TABLE A-continued

| Compound | Structure |
|---|---|
| 29 | 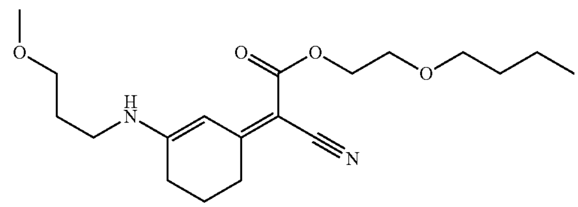 [SMILES: CCCCOCCOC(=O)/C(C#N)=C1\C=C(NCCCOC)CCC1] |
| 30 | 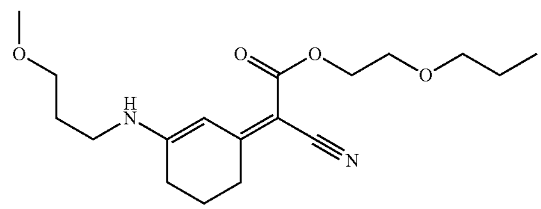 [SMILES: CCCOCCOC(=O)/C(C#N)=C1\C=C(NCCCOC)CCC1] |
| 31 | 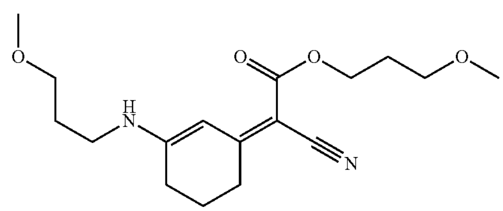 [SMILES: COCCCNC1=C/C(=C(/C#N)C(=O)OCCCOC)CCC1] |
| 32 | 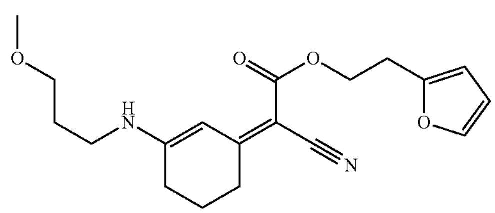 [SMILES: COCCCNC1=C/C(=C(/C#N)C(=O)OCCc2ccco2)CCC1] |
| 33 | 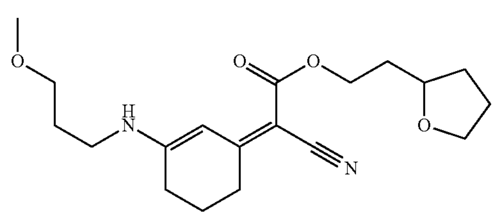 [SMILES: COCCCNC1=C/C(=C(/C#N)C(=O)OCCC2CCCO2)CCC1] |
| 34 | 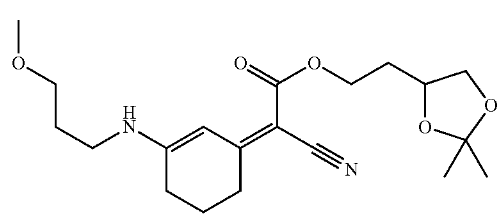 [SMILES: COCCCNC1=C/C(=C(/C#N)C(=O)OCCC2COC(C)(C)O2)CCC1] |
| 35 | 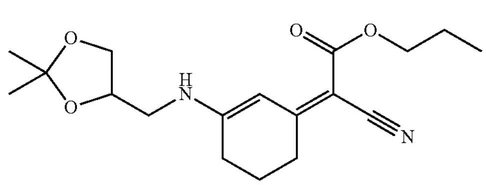 [SMILES: CCCOC(=O)/C(C#N)=C1\C=C(NCC2COC(C)(C)O2)CCC1] |

TABLE A-continued

| Compound | Structure |
|---|---|
| 36 | 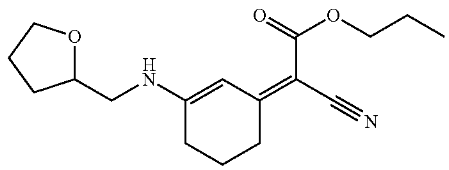 [SMILES: CCCOC(=O)/C(C#N)=C1\C=C(NCC2CCCO2)CCC1] |
| 37 | 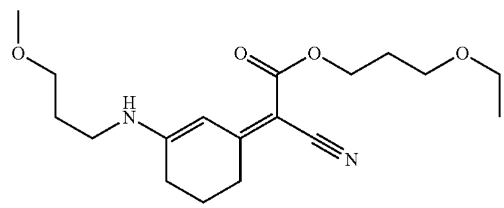 [SMILES: CCOCCCOC(=O)/C(C#N)=C1\C=C(NCCCOC)CCC1] |
| 38 | 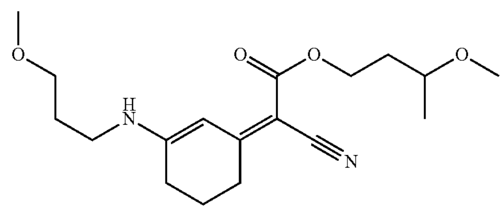 [SMILES: COCCCNC1=C/C(=C(/C#N)C(=O)OCCC(C)OC)CCC1] |
| 39 | 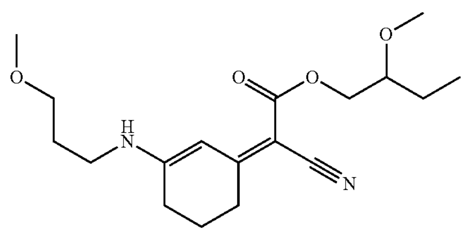 [SMILES: CCC(COC(=O)/C(C#N)=C1\C=C(NCCCOC)CCC1)OC] |
| 40 | 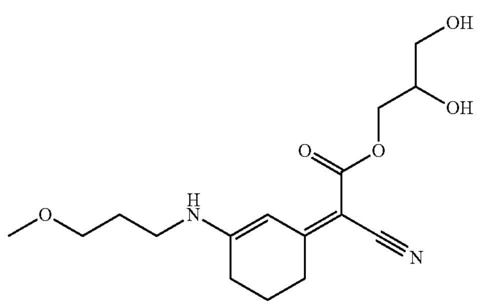 [SMILES: COCCCNC1=C/C(=C(/C#N)C(=O)OCC(O)CO)CCC1] |
| 41 | 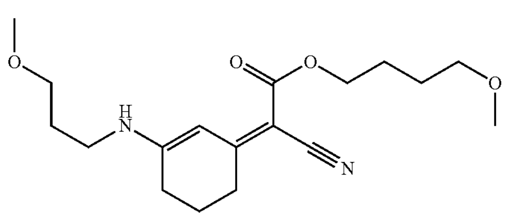 [SMILES: COCCCCOC(=O)/C(C#N)=C1\C=C(NCCCOC)CCC1] |
| 42 | 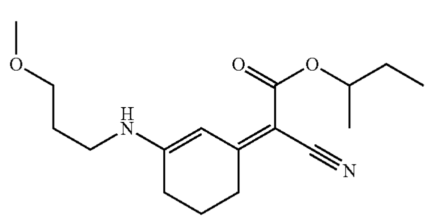 [SMILES: CCC(C)OC(=O)/C(C#N)=C1\C=C(NCCCOC)CCC1] |

TABLE A-continued

| Compound | Structure |
|---|---|
| 43 | 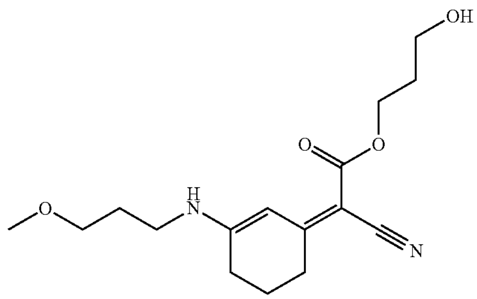 [SMILES: COCCCNC1=C/C(=C(/C#N)C(=O)OCCCO)CCC1] |
| 44 | 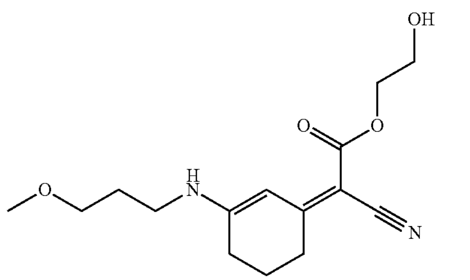 [SMILES: COCCCNC1=C/C(=C(/C#N)C(=O)OCCO)CCC1] |
| 45 | 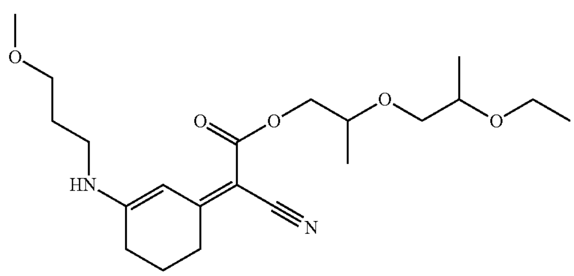 [SMILES: CCOC(C)COC(C)COC(=O)/C(C#N)=C1\C=C(NCCCOC)CCC1] |
| 46 | 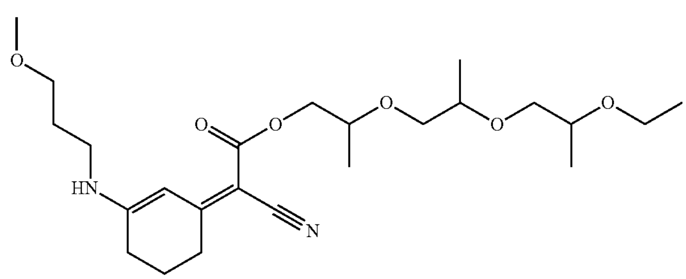 [SMILES: CCOC(C)COC(C)COC(C)COC(=O)/C(C#N)=C1\C=C(NCCCOC)CCC1] |
| 47 | 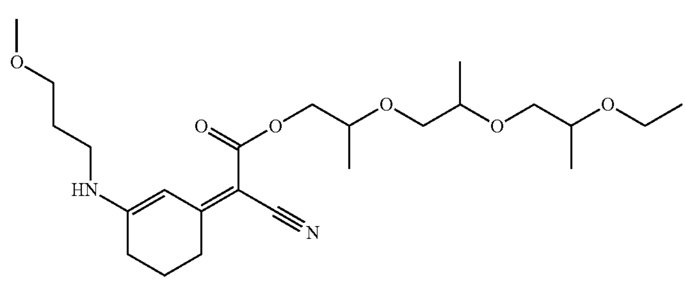 [SMILES: CCOC(C)COC(C)COC(C)COC(=O)/C(C#N)=C1\C=C(NCCCOC)CCC1] |

According to a particularly preferred form of the invention, use will be made of a merocyanine family corresponding to formula (3) below, and also the E/E- or E/Z-geometrical isomer forms thereof:

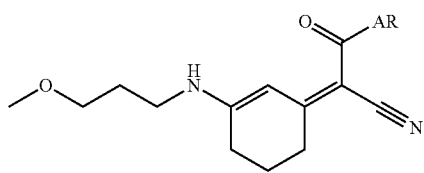

(3)

in which:

A is —O— or —NH;

R is a $C_1$-$C_{22}$ alkyl group, a $C_2$-$C_{22}$ alkenyl group, a $C_2$-$C_{22}$ alkynyl group, a $C_3$-$C_{22}$ cycloalkyl group or a $C_3$-$C_{22}$ cycloalkenyl group, the said groups possibly being interrupted with one or more O.

The merocyanine compounds of the invention may be in their E/E- or E/Z-geometrical isomer forms.

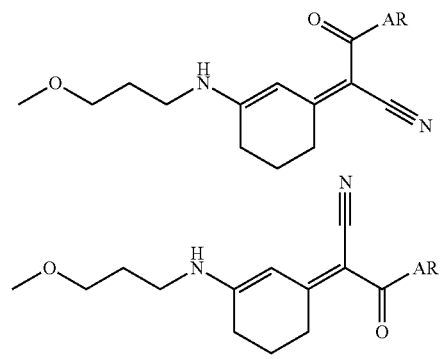

The even more preferential compounds of formula (3) are those in which:

A is —O—; R is a $C_1$-$C_{22}$ alkyl, which may be interrupted with one or more O.

Among the compounds of formula (3), use will be made more particularly of those chosen from the following group, and also the E/E- or E/Z-geometrical isomer forms thereof:

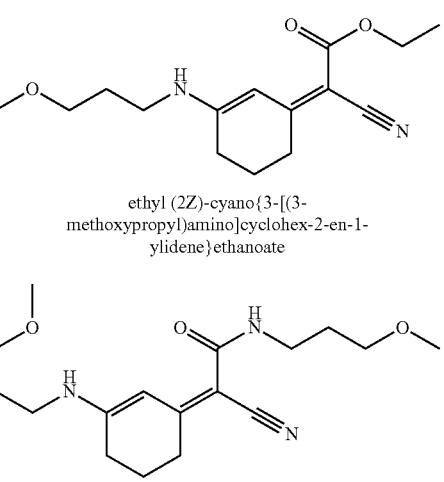

ethyl (2Z)-cyano{3-[(3-methoxypropyl)amino]cyclohex-2-en-1-ylidene}ethanoate  14

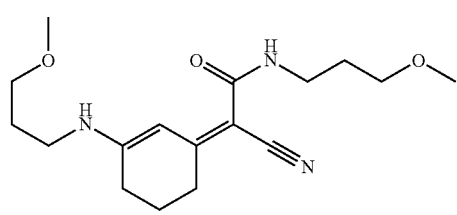

(2Z)-2-cyano-N-(3-methoxypropyl)-2-{3-[(3-methoxypropyl)amino]cyclohex-2-en-1-ylidene}ethanamide  15

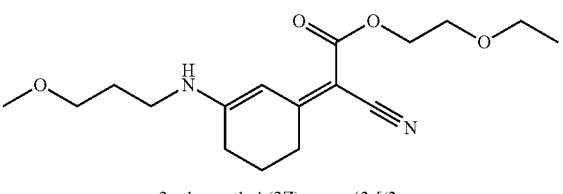

2-ethoxyethyl (2Z)-cyano{3-[(3-methoxypropyl)amino]cyclohex-2-en-1-ylidene}ethanoate  25

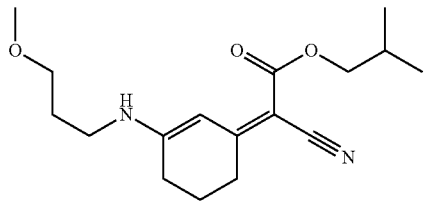

2-methylpropyl (2Z)-cyano{3-[(3-methoxypropyl)amino]cyclohex-2-en-1-ylidene}ethanoate  27

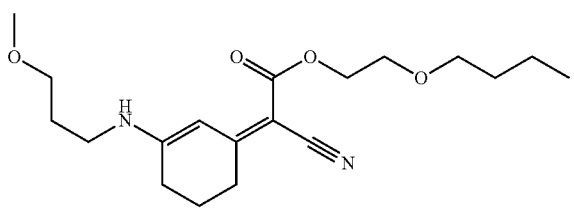

2-butoxyethyl (2Z)-cyano{3-[(3-methoxypropyl)amino]cyclohex-2-en-1-ylidene}ethanoate  29

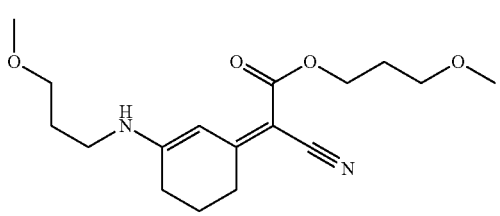

3-methoxypropyl (2Z)-cyano{3-[(3-methoxypropyl)amino]cyclohex-2-en-1-ylidene}ethanoate  31

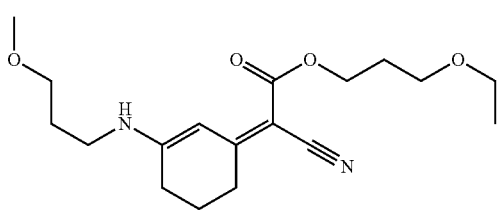

3-ethoxypropyl (2Z)-cyano{3-[(3-methoxypropyl)amino]cyclohex-2-en-1-ylidene}ethanoate  37

According to a more particularly preferred mode of the invention, use will be made of the compound 2-ethoxyethyl (2Z)-cyano{3-[(3-methoxypropyl)amino]cyclohex-2-en-1-ylidene}ethanoate (25) in its E/E and/or E/Z geometrical configuration.

The E/Z form has the following structure:

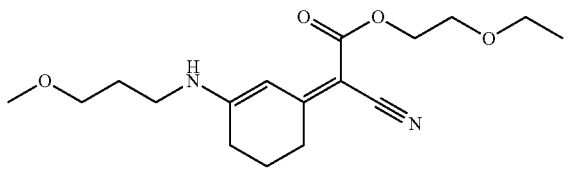 [SMILES: CCOCCOC(=O)/C(C#N)=C1\C=C(NCCCOC)CCC1]

The E/E form has the following structure:

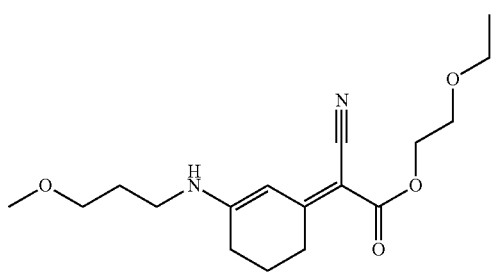 [SMILES: CCOCCOC(=O)/C(C#N)=C1/C=C(NCCCOC)CCC1]

The screening merocyanines in accordance with the invention may be present in the compositions according to the invention in a concentration ranging from 0.1% to 10% by weight and preferentially from 0.2% to 5% by weight relative to the total weight of the composition.

The compounds of formulae (1) and (2) and especially of formula (3) may be prepared according to known processes, as described, for example, in J. Org. Chem. USSR (English translation) 26(8), p. 1562f (1990); J. Heterocycl. Chem. 33(3), p. 763-766 (1996); Khimiya Geterotsiklicheskikh Soedinenii 11, p. 1537-1543 (1984); Khimiya Geterotsiklicheskikh Soedinenii 3, p. 397-404 (1982); Chem. Heterocycl. Comp. (English translation) 24(8), 914-919 (1988) and in Synthetic Communications Vol. 33, No. 3, 2003, p 367-371.

The synthesis of the compounds used in the present invention is also described in US 2003/0 181 483 A1, WO 02/34710, Eur. J. Org. Chem. 2003, 2250-2253, J. Med. Chem. 1996, 39, 1112-1124 and J. Org. Chem., Vol. 37, No. 8, 1972, 1141-1145 as follows:

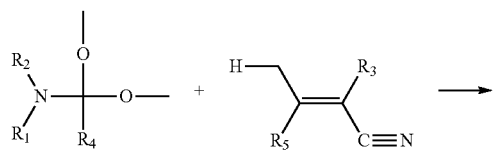

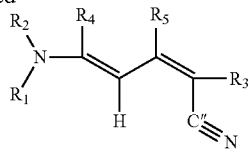

CH-acid vinylogen compounds are reacted with amide acetals.

In document J. Heterocyclic Chem., 27, 1990, 1143-1151, aminoacrylic acid esters or aminoacrylonitriles are reacted with ethoxymethylenecyanoacetates in ethanol to form the corresponding compounds of the present invention.

The compounds of formula (1) or (2) in which $R_4$ and $R_5$, on the one hand, or $R_9$ and $R_{10}$, on the other hand, together form a carbocyclic ring containing 6 carbon atoms, respectively, may be prepared according to the protocols described in Pat. Appl. WO 2007/071 582, in IP.com Journal (2009), 9(5A), 29-30 IPCOM000182396D under the title "Process for producing 3-amino-2-cyclohexan-1-ylidene compounds" and in U.S. Pat. No. 4,749,643 on column 13, line 66-column 14, line 57 and the references cited in this regard.

Amide Compounds

The amide compounds in accordance with the invention correspond to formula (I) below:

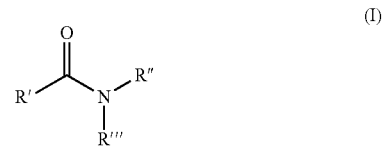

(I)

in which

R' is a linear or branched, saturated or unsaturated $C_4$-$C_{22}$ alkyl radical and R" and R''', which may be identical or different, are linear or branched $C_2$-$C_{10}$ alkyl radicals, optionally substituted with a hydroxyl group;

R' and R''' may form with the nitrogen atom and the carbonyl group a caprolactam ring;

R" and R''' may form with the nitrogen atom to which they are attached a heterocycle comprising from 4 to 6 carbon atoms, which may contain an oxygen atom.

The radicals R', R" and R''' may be identical or different.

The fatty amides of formula (I) in accordance with the invention are known per se and are especially described in U.S. Pat. No. 5,206,225 and in patent application US 2008/0 269 355.

As examples of amide compounds of formula (I), mention may be made of the following compounds:

| CAS No. | NAME | Structure |
|---|---|---|
| 14433-76-2 | N,N Dimethylcapramide | 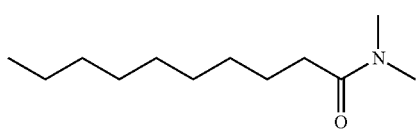 |

-continued

| CAS No. | NAME | Structure |
|---|---|---|
| 1118-92-9 | N,N Dimethyl caprylamide | 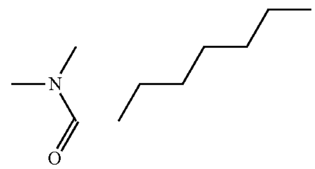 |
| 142-78-9 | Lauryl Monoethanolamide | 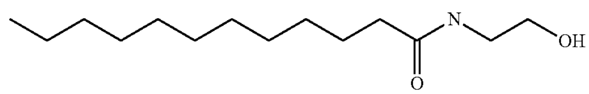 [SMILES: CCCCCCCCCCCC(=O)NCCO] |
| 111-57-9 | Stearyl Ethanolamide | 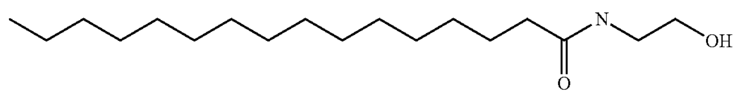 [SMILES: CCCCCCCCCCCCCCCC(=O)NCCO] |
| 111-58-0 | Oleyl Ethanolamide | 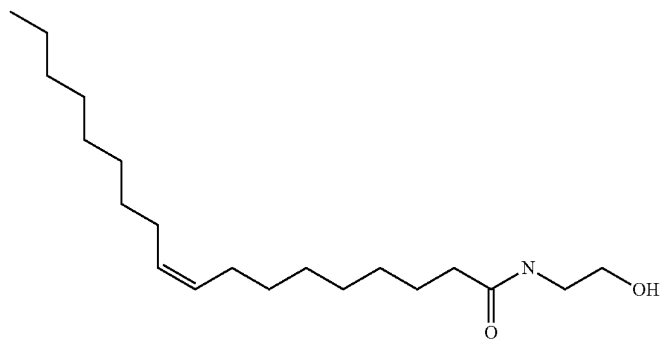 [SMILES: CCCCCCCC/C=C\CCCCCCCC(=O)NCCO] |
| 111-05-7 | Oleyl Monoisopropanolamide | 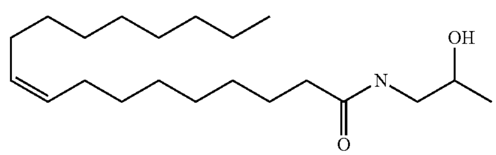 [SMILES: CCCCCCCC/C=C\CCCCCCCC(=O)NCC(C)O] |
| 120-40-1 | Lauryl Diethanolamide | 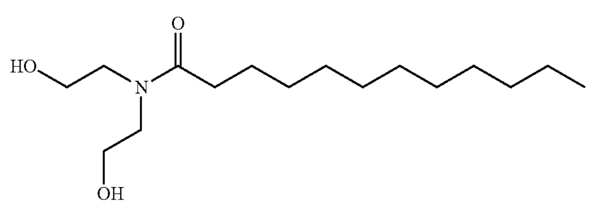 [SMILES: CCCCCCCCCCCC(=O)N(CCO)CCO] |
| 7545-23-5 | Myristyl Diethanolamide | 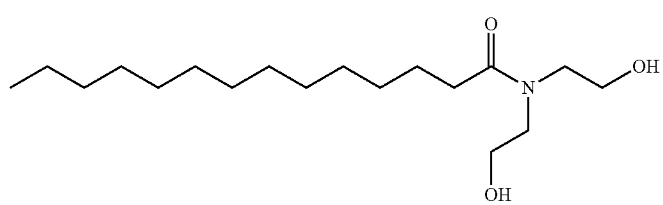 [SMILES: CCCCCCCCCCCCCC(=O)N(CCO)CCO] |
| 3352-87-2 | N,N-Diethyldodecanamide | 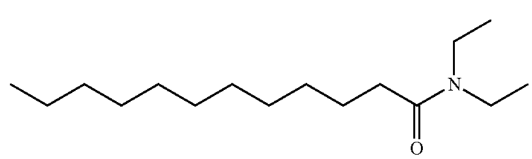 [SMILES: CCCCCCCCCCCC(=O)N(CC)CC] |
| 3007-53-2 | N,N-Dimethyldodecanamide | 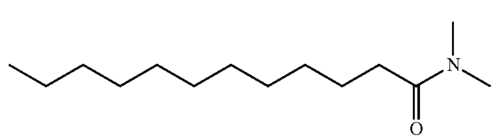 [SMILES: CCCCCCCCCCCC(=O)N(C)C] |

| CAS No. | NAME | Structure |
|---|---|---|
| 2602-61-1 | N,N-diethyldecanamide | 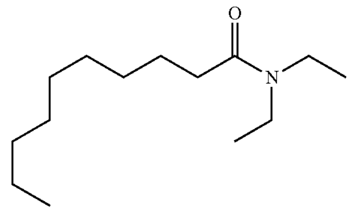 [SMILES: CCCCCCCCCC(=O)N(CC)CC] |
| 70974-45-7 | 1-dodecanoyl pyrrolidine | 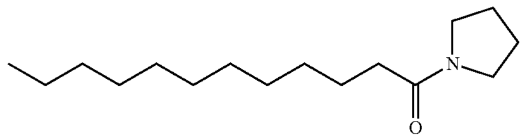 [SMILES: CCCCCCCCCCCC(=O)N1CCCC1] |
| 996-97-4: | N,N-diethyloctanamide | 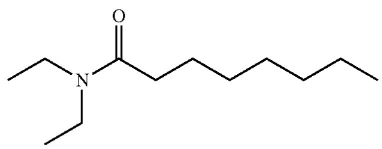 |
| 59227-89-3 | N-lauryl caprolactame | 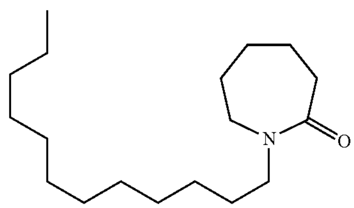 [SMILES: CCCCCCCCCCCCN1CCCCCC1=O] |
| 59227-88-2 | N-octyl caprolactame | 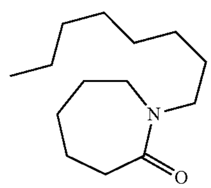 [SMILES: CCCCCCCCN1CCCCCC1=O] |
| 17598-10-6 | N-hexanoylmorpholine | 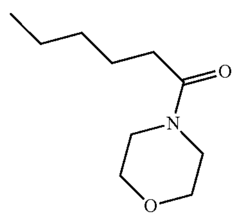 |
| 5299-65-0 | N-decanoylmorpholine | 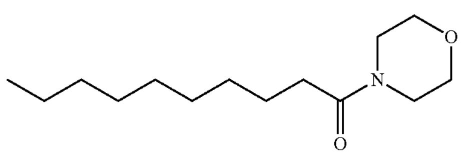 [SMILES: CCCCCCCCCC(=O)N1CCOCC1] |

The preferred amides of the invention of formula (I) are those for which:

R' is a linear or branched $C_6$-$C_{16}$ alkyl; and

R" and R'" are hydrogen, or a methyl or an ethyl optionally substituted with a hydroxyl.

The amides that are even more preferred of the invention of formula (I) are those in which R' is a linear or branched $C_6$-$C_{12}$ alkyl; and R" and R'" are a methyl or an ethyl.

Among the $C_6$-$C_{12}$ alkyl radicals, mention may be made of hexyl, octyl, capryl, lauryl, myristyl, dodecyl, decyl, stearyl and oleyl radicals.

Among the heterocycles formed by the radicals R" and R'" with the nitrogen atom to which they are attached, mention may be made of pyrrolidine, morpholine and azacycloheptane.

Among the more particularly preferential compounds, the following will be used:

N,N-dimethylcapramide (CAS No. 14433-76-2) sold by the company Haohua Industry, or under the name Hallcomid® M-10 by the company Stepan, N,N-dimethylcaprylamide (CAS No. 1118-92-9) sold, for example, by the companies BOO Sciences or Chemos GmbH, or mixtures thereof, for instance the product sold under the name Hallcomid® M-8-10 by the company Stepan.

N,N-Dimethylcapramide will be used even more particularly.

The amide compounds according to the invention are preferably present in the compositions according to the invention in a concentration ranging from 0.1% to 50% by weight, preferentially from 0.2% to 30% by weight and even more preferentially from 0.3% to 15% by weight relative to the total weight of the composition.

Oily Phase

The compositions in accordance with the invention comprise at least one oily phase.

For the purposes of the invention, the term "oily phase" means a phase comprising at least one oil and all of the liposoluble and lipophilic ingredients and the fatty substances used for the formulation of the compositions of the invention.

The term "oil" means any fatty substance which is in liquid form at room temperature (20-25° C.) and at atmospheric pressure (760 mmHg).

The oily phase may comprise, in addition to the merocyanine screening agent(s) and, where appropriate, the additional lipophilic screening agents and the amide-based compound(s) according to the invention, at least one volatile or non-volatile hydrocarbon-based oil and/or one volatile and/or non-volatile silicone oil and/or one volatile and/or non-volatile fluoro oil.

For the purposes of the present invention, the term "silicone oil" means an oil comprising at least one silicon atom, and especially at least one Si—O group.

The term "hydrocarbon-based oil" means an oil comprising mainly hydrogen and carbon atoms.

The term "fluoro oil" means an oil comprising at least one fluorine atom.

For the purposes of the invention, the term "volatile oil" means an oil that is capable of evaporating on contact with the skin or the keratin fibre in less than one hour, at room temperature and atmospheric pressure. The volatile oil(s) of the invention are volatile cosmetic oils which are liquid at room temperature and which have a non-zero vapour pressure, at room temperature and atmospheric pressure, ranging in particular from 0.13 Pa to 40 000 Pa ($10^{-3}$ to 300 mmHg), in particular ranging from 1.3 Pa to 13 000 Pa (0.01 to 100 mmHg) and more particularly ranging from 1.3 Pa to 1300 Pa (0.01 to 10 mmHg).

The term "non-volatile oil" means an oil which remains on the skin or the keratin fibre, at room temperature and atmospheric pressure, for at least several hours and which in particular has a vapour pressure of less than $10^{-3}$ mmHg (0.13 Pa).

Hydrocarbon-Based Oils

As non-volatile hydrocarbon-based oils that may be used according to the invention, mention may be made especially of:

(i) hydrocarbon-based oils of plant origin, such as glyceride triesters, which are generally triesters of fatty acids and of glycerol, the fatty acids of which can have varied chain lengths from $C_4$ to $C_{24}$, it being possible for these chains to be saturated or unsaturated and linear or branched; these oils are in particular wheat germ oil, sunflower oil, grape seed oil, sesame oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin seed oil, marrow oil, blackcurrant oil, evening primrose oil, millet oil, barley oil, quinoa oil, rye oil, safflower oil, candlenut oil, passionflower oil and musk rose oil; or also caprylic/capric acid triglycerides, such as those sold by Stéarineries Dubois or those sold under the names Miglyol 810®, 812® and 818® by Dynamit Nobel;

(ii) synthetic ethers containing from 10 to 40 carbon atoms;

(iii) linear or branched hydrocarbons of mineral or synthetic origin, such as petroleum jelly, polydecenes, hydrogenated polyisobutene such as Parleam, and squalane, and mixtures thereof;

(iv) synthetic esters, for instance oils of formula RCOOR' in which R represents a linear or branched fatty acid residue containing from 1 to 40 carbon atoms and R' represents a hydrocarbon-based chain that is especially branched, containing from 1 to 40 carbon atoms on condition that R+R' is ≥10, for instance Purcellin oil (cetearyl octanoate), isopropyl myristate, isopropyl palmitate, $C_{12}$-$C_{15}$ alkyl benzoate, such as the product sold under the trade name Finsolv TN® or Witconol TN® by Witco or Tegosoft TN® by Evonik Goldschmidt, 2-ethylphenyl benzoate, such as the commercial product sold under the name X-Tend 226® by ISP, isopropyl lanolate, hexyl laurate, diisopropyl adipate, isononyl isononanoate, oleyl erucate, 2-ethylhexyl palmitate, isostearyl isostearate, diisopropyl sebacate, such as the product sold under the name of "Dub Dis" by Stearinerie Dubois, octanoates, decanoates or ricinoleates of alcohols or polyalcohols, such as propylene glycol dioctanoate; hydroxylated esters, such as isostearyl lactate or diisostearyl malate; and pentaerythritol esters; citrates or tartrates, such as di(linear $C_{12}$-$C_{13}$ alkyl) tartrates, such as those sold under the name Cosmacol ETI® by Enichem Augusta Industriale, and also di(linear $C_{14}$-$C_{15}$ alkyl) tartrates, such as those sold under the name Cosmacol ETL® by the same company; or acetates;

(v) fatty alcohols that are liquid at room temperature, containing a branched and/or unsaturated carbon-based chain containing from 12 to 26 carbon atoms, for instance octyldodecanol, isostearyl alcohol, oleyl alcohol, 2-hexyldecanol, 2-butyloctanol or 2-undecylpentadecanol;

(vi) higher fatty acids, such as oleic acid, linoleic acid or linolenic acid;

(vii) carbonates, such as dicaprylyl carbonate, such as the product sold under the name Cetiol CC® by Cognis;

and mixtures thereof.

Preference will more particularly be given, among the non-volatile hydrocarbon-based oils that may be used according to the invention, to glyceride triesters and in particular to caprylic/capric acid triglycerides, synthetic esters and in particular isononyl isononanoate, oleyl erucate, $C_{12}$-$C_{15}$ alkyl benzoate, 2-ethylphenyl benzoate and fatty alcohols, in particular octyldodecanol.

Mention may in particular be made, as volatile hydrocarbon-based oils that may be used according to the invention, of hydrocarbon-based oils containing from 8 to 16 carbon atoms and in particular of branched $C_8$-$C_{16}$ alkanes, such as $C_8$-$C_{16}$ isoalkanes of petroleum origin (also known as isoparaffins), such as isododecane (also known as 2,2,4,4,6-pentamethylheptane), isodecane or isohexadecane, the oils sold under the Isopar or Permethyl trade names, branched $C_8$-$C_{16}$ esters, isohexyl neopentanoate, and mixtures thereof.

Mention may also be made of the alkanes described in Cognis patent applications WO 2007/068 371 or WO 2008/

155 059 (mixtures of distinct alkanes differing by at least one carbon). These alkanes are obtained from fatty alcohols, which are themselves obtained from coconut or palm oil. Mention may be made of the mixtures of n-undecane ($C_{11}$) and n-tridecane ($C_{13}$) obtained in Examples 1 and 2 of patent application WO 2008/155 059 from the company Cognis. Mention may also be made of n-dodecane ($C_{12}$) and n-tetradecane ($C_{14}$) sold by Sasol under the respective references Parafol 12-97 and Parafol 14-97®, and also mixtures thereof.

Use may also be made of other volatile hydrocarbon-based oils, such as petroleum distillates, in particular those sold under the name Shell Solt® by Shell. According to one embodiment, the volatile solvent is chosen from volatile hydrocarbon-based oils containing from 8 to 16 carbon atoms, and mixtures thereof.

b) Silicone Oils

The non-volatile silicone oils may be chosen in particular from non-volatile polydimethylsiloxanes (PDMSs), polydimethylsiloxanes comprising alkyl or alkoxy groups which are pendent and/or at the end of the silicone chain, which groups each contain from 2 to 24 carbon atoms, or phenyl silicones, such as phenyl trimethicones, phenyl dimethicones, phenyl(trimethylsiloxy)diphenylsiloxanes, diphenyl dimethicones, diphenyl(methyldiphenyl)trisiloxanes or (2-phenylethyl)trimethylsiloxysilicates.

Examples of volatile silicone oils that may be mentioned include volatile linear or cyclic silicone oils, especially those with a viscosity≤8 centistokes ($8 \times 10^{-6}$ m$^2$/s) and especially containing from 2 to 7 silicon atoms, these silicones optionally comprising alkyl or alkoxy groups containing from 1 to 10 carbon atoms. As volatile silicone oils that may be used in the invention, mention may be made especially of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

Mention may also be made of the volatile linear alkyltrisiloxane oils of general formula (I):

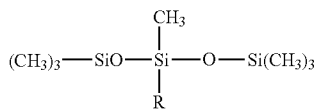

where R represents an alkyl group comprising from 2 to 4 carbon atoms, one or more hydrogen atoms of which may be substituted with a fluorine or chlorine atom.

Among the oils of general formula (I), mention may be made of:
3-butyl-1,1,1,3,5,5,5-heptamethyltrisiloxane,
3-propyl-1,1,1,3,5,5,5-heptamethyltrisiloxane, and
3-ethyl-1,1,1,3,5,5,5-heptamethyltrisiloxane,
corresponding to the oils of formula (I) for which R is, respectively, a butyl group, a propyl group or an ethyl group.

Fluoro Oils

Use may also be made of volatile fluoro oils, such as nonafluoromethoxybutane, decafluoropentane, tetradecafluorohexane, dodecafluoropentane, and mixtures thereof.

An oily phase according to the invention may also comprise other fatty substances, mixed with or dissolved in the oil.

Another fatty substance that may be present in the oily phase may be, for example:

a fatty acid chosen from fatty acids comprising from 8 to 30 carbon atoms, such as stearic acid, lauric acid, palmitic acid and oleic acid;

a wax chosen from waxes such as lanolin, beeswax, carnauba or candelilla wax, paraffin waxes, lignite waxes, microcrystalline waxes, ceresin or ozokerite, or synthetic waxes, such as polyethylene waxes or Fischer-Tropsch waxes;

a gum chosen from silicone gums (dimethiconol);

a pasty compound, such as polymeric or non-polymeric silicone compounds, esters of a glycerol oligomer, arachidyl propionate, fatty acid triglycerides and derivatives thereof;

and mixtures thereof.

Preferably, the overall oily phase, including all the lipophilic substances of the composition that are capable of being dissolved in this same phase, represents from 5% to 95% by weight and preferably from 10% to 80% by weight, relative to the total weight of the composition.

Aqueous Phase

The compositions according to the invention may also comprise at least one aqueous phase.

The aqueous phase contains water, and optionally other water-soluble or water-miscible organic solvents.

An aqueous phase that is suitable for use in the invention may comprise, for example, a water chosen from a water from a natural source, such as water from La Roche-Posay, water from Vittel or water from Vichy, or a floral water.

The water-soluble or water-miscible solvents that are suitable for use in the invention comprise short-chain, for example $C_1$-$C_4$, monoalcohols such as ethanol and isopropanol; diols or polyols, for instance ethylene glycol, 1,2-propylene glycol, 1,3-butylene glycol, hexylene glycol, diethylene glycol, dipropylene glycol, 2-ethoxyethanol, diethylene glycol monomethyl ether, triethylene glycol monomethyl ether, glycerol and sorbitol, and mixtures thereof.

According to a preferred embodiment, use may be made more particularly of ethanol, propylene glycol or glycerol, and mixtures thereof.

According to a particular form of the invention, the overall aqueous phase, including all the hydrophilic substances of the composition that are capable of being dissolved in this same phase, represents from 5% to 95% by weight and preferentially from 10% to 80% by weight relative to the total weight of the composition.

Additives a) Additional UV-Screening Agents

The compositions according to the invention may also contain one or more additional UV-screening agents chosen from hydrophilic, lipophilic or insoluble organic UV-screening agents and/or one or more mineral pigments. Preferentially, it will consist of at least one hydrophilic, lipophilic or insoluble organic UV-screening agent.

The term "hydrophilic UV-screening agent" means any cosmetic or dermatological organic or mineral compound for screening out UV radiation which is capable of being fully dissolved in molecular form in a liquid aqueous phase or of being dissolved in colloidal form (for example in micellar form) in a liquid aqueous phase.

The term "lipophilic screening agent" means any cosmetic or dermatological organic or mineral compound for screening out UV radiation, which can be fully dissolved in molecular state in a liquid fatty phase or which can be dissolved in colloidal form (for example in micellar form) in a liquid fatty phase.

The term "insoluble UV-screening agent" means any cosmetic or dermatological organic or mineral compound for screening out UV radiation which has a water-solubility of less than 0.5% by weight and a solubility of less than 0.5% by weight in the majority of organic solvents such as liquid paraffin, fatty alkyl benzoates and fatty acid triglycerides, for example Miglyol 812® sold by the company Dynamit Nobel. This solubility, determined at 70° C., is defined as the amount of product in solution in the solvent at equilibrium with an excess of solid in suspension after returning to room temperature. It may be readily evaluated in the laboratory.

The additional organic UV-screening agents are chosen in particular from cinnamic compounds; anthranilate compounds; salicylic compounds; dibenzoylmethane compounds; benzylidenecamphor compounds; benzophenone compounds; β,β-diphenylacrylate compounds; triazine compounds; benzotriazole compounds; benzalmalonate compounds, in particular those cited in U.S. Pat. No. 5,624,663; benzimidazole derivatives; imidazolin compounds; bis-benzoazolyl compounds, as described in patents EP 669 323 and U.S. Pat. No. 2,463,264; p-aminobenzoic acid (PABA) compounds; methylenebis(hydroxyphenylbenzotriazole) compounds, such as described in patent applications U.S. Pat. No. 5,237,071, U.S. Pat. No. 5,166,355, GB 2 303 549, DE 197 26 184 and EP 893 119; benzoxazole compounds, as described in patent applications EP 0 832 642, EP 1 027 883, EP 1 300 137 and DE 101 62 844; screening polymers and screening silicones, such as those described in particular in patent application WO 93/04665; α-alkylstyrene-based dimers, such as those described in patent application DE 198 55 649; 4,4-diarylbutadiene compounds, as described in patent applications EP 0 967 200, DE 197 46 654, DE 197 55 649, EP-A-1 008 586, EP 1 133 980 and EP 133 981, and mixtures thereof.

As examples of organic photoprotective agents, mention may be made of those denoted hereinbelow under their INCI name:

Cinnamic Compounds:
Ethylhexyl Methoxycinnamate, sold in particular under the trade name Parsol MCX® by DSM Nutritional Products,
Isopropyl Methoxycinnamate,
Isoamyl p-methoxycinnamate sold under the trade name Neo Heliopan E 1000® by Symrise,
DEA Methoxycinnamate,
Diisopropyl Methyl Cinnamate,
Glyceryl Ethylhexanoate Dimethoxycinnamate.

Dibenzoylmethane Compounds:
Butylmethoxydibenzoylmethane sold in particular under the trade name Parsol 1789® by DSM Nutritional Products,
Isopropyldibenzoylmethane.

Para-Aminobenzoic Compounds:
PABA,
Ethyl PABA,
Ethyl Dihydroxypropyl PABA,
Ethylhexyl Dimethyl PABA, sold in particular under the name Escalol 507® by ISP,
Glyceryl PABA,
PEG-25 PABA, sold under the name Uvinul P 25® by BASF.

Salicylic Compounds:
Homosalate, sold under the name Eusolex HMS® by Rona/EM Industries,
Ethylhexyl Salicylate, sold under the name Neo Heliopan OS® by Symrise,
Dipropylene Glycol Salicylate, sold under the name Dipsal® by Scher,
TEA Salicylate, sold under the name Neo Heliopan TS® by Symrise.

β,β-Diphenylacrylate Compounds:
Octocrylene, sold in particular under the trade name Uvinul N 539® by BASF,
Etocrylene, sold in particular under the trade name Uvinul N 35® by BASF.

Benzophenone Compounds:
Benzophenone-1, sold under the trade name Uvinul 400® by BASF,
Benzophenone-2, sold under the trade name Uvinul D 50® by BASF,
Benzophenone-3 or Oxybenzone, sold under the trade name Uvinul M 40® by BASF,
Benzophenone-4, sold under the trade name Uvinul MS 40® by BASF,
Benzophenone-5,
Benzophenone-6, sold under the trade name Helisorb 11® by Norquay,
Benzophenone-8, sold under the trade name Spectra-Sorb UV-24® by American Cyanamid,
Benzophenone-9, sold under the trade name Uvinul DS 49® by BASF,
Benzophenone-12,
n-Hexyl 2-(4-diethylamino-2-hydroxybenzoyl)benzoate, sold under the trade name Uvinul A Plus® or, as a mixture with octyl methoxycinnamate, under the trade name Uvinul A Plus B® by BASF,
1,1'-(1,4-Piperazinediyl)bis[1-[2-[4-(diethylamino)-2-hydroxybenzoyl]phenyl]methanone] (CAS 919803-06-8), such as described in patent application WO 2007/071 584; this compound advantageously being used in micronized form (mean size of 0.02 to 2 μm), which may be obtained, for example, according to the micronization process described in patent applications GB-A-2 303 549 and EP-A-893 119, and in particular in the form of an aqueous dispersion.

Benzylidenecamphor Compounds:
3-Benzylidene Camphor, manufactured under the name Mexoryl SD® by Chimex,
4-Methylbenzylidene Camphor, sold under the name Eusolex 6300® by Merck,
Benzylidene Camphor Sulfonic Acid, manufactured under the name Mexoryl SL® by Chimex,
Camphor Benzalkonium Methosulfate, manufactured under the name Mexoryl SO® by Chimex,
Terephthalylidene Dicamphor Sulfonic Acid, manufactured under the name Mexoryl SX® by Chimex,
Polyacrylamidomethyl Benzylidene Camphor, manufactured under the name Mexoryl SW® by Chimex.

Phenylbenzimidazole Compounds:
Phenylbenzimidazole Sulfonic Acid, sold in particular under the trade name Eusolex 232® by Merck.

Bis-Benzazolyl Compounds:
Disodium Phenyl Dibenzimidazole Tetrasulfonate, sold under the trade name Neo Heliopan AP® by Haarmann and Reimer.

Phenylbenzotriazole Compounds:
Drometrizole Trisiloxane, sold under the name Silatrizole® by Rhodia Chimie.

Methylenebis(Hydroxyphenylbenzotriazole) Compounds:
Methylenebis(benzotriazolyl)tetramethylbutylphenol especially in solid form, for instance the product sold under the trade name Mixxim BB/100® by Fairmount Chemical or in the form of an aqueous dispersion of micronized particles with a mean particle size ranging from 0.01 to 5 μm, more preferentially from 0.01 to 2 μm and more particularly from 0.020 to 2 µm with at least one alkylpolyglycoside surfactant of structure $C_nH_{2n+1}O(C_6H_{10}O_5)_xH$, in which n is an integer from 8 to 16 and x is the mean degree of polymerization of the $(C_6H_{10}C_5)$ unit and ranges from 1.4 to 1.6, such as described in patent GB-A-2 303 549, sold in particular under the trade name Tinosorb M® by BASF, or in the form of an aqueous dispersion of micronized particles with a mean particle size ranging from 0.02 to 2 µm, more preferably from 0.01 to 1.5 µm and more particularly from 0.02 to 1 µm, in the presence of at least one polyglyceryl mono($C_8$-$C_{20}$) alkyl ester with a degree of glycerol polymerization of at least 5, such as the aqueous dispersions described in patent application WO 2009/063 392.

Triazine Compounds:
- Bis-Ethylhexyloxyphenol Methoxyphenyl Triazine, sold under the trade name Tinosorb S® by BASF,
- Ethylhexyl Triazone, sold in particular under the trade name Uvinul T150® by BASF,
- Diethylhexyl Butamido Triazone, sold under the trade name Uvasorb HEB® by Sigma 3V,
- 2,4,6-tris(dineopentyl 4'-aminobenzalmalonate)-s-triazine,
- 2,4,6-tris(diisobutyl 4'-aminobenzalmalonate)-s-triazine;
- 2,4-bis(n-butyl 4'-aminobenzoate)-6-(aminopropyltrisiloxane)-s-triazine,
- 2,4-bis(dineopentyl 4'-aminobenzalmalonate)-6-(n-butyl 4'-aminobenzoate)-s-triazine,
- symmetrical triazine screening agents substituted with naphthalenyl groups or polyphenyl groups described in U.S. Pat. No. 6,225,467, patent application WO 2004/085 412 (see compounds 6 and 9) or the document "Symmetrical Triazine Derivatives", IP.COM IPCOM000031257 Journal, INC, West Henrietta, N.Y., US (20 Sep. 2004), in particular 2,4,6-tris(diphenyl) triazine and 2,4,6-tris(terphenyl)triazine, which is also mentioned in patent applications WO 06/035 000, WO 06/034 982, WO 06/034 991, WO 06/035 007, WO 2006/034 992 and WO 2006/034 985, these compounds advantageously being used in micronized form (mean particle size of 0.02 to 3 µm), which may be obtained, for example, according to the micronization process described in patent applications GB-A-2 303 549 and EP-A-893 119, and in particular in the form of an aqueous dispersion;
- silicone triazines substituted with two aminobenzoate groups, as described in patent EP 0 841 341, in particular 2,4-bis(n-butyl 4'-aminobenzalmalonate)-6-[(3-{1,3,3,3-tetramethyl-1-[(trimethylsilyl)oxy]disiloxanyl}propyl)amino]-s-triazine.

Anthranilic Compounds:
Menthyl Anthranilate, sold under the trade name Neo Heliopan MAO by Symrise.

Imidazoline Compounds:
Ethylhexyl dimethoxybenzylidene dioxoimidazoline propionate.

Benzalmalonate Compounds:
Polyorganosiloxane comprising benzalmalonate functional groups, such as Polysilicone-15, sold under the trade name Parsol SLXO by Hoffmann-LaRoche.

4,4-Diarylbutadiene Compounds:
1,1-Dicarboxy(2,2'-dimethylpropyl)-4,4-diphenylbutadiene.

Benzoxazole Compounds:
2,4-Bis[4-[5-(1,1-dimethylpropyl)benzoxazol-2-yl]phenylimino]-6-[(2-ethylhexyl)imino]-1,3,5-triazine, sold under the name of Uvasorb K2A® by Sigma 3V.

The preferred organic screening agents are chosen from:
Ethylhexyl Methoxycinnamate,
Ethylhexyl salicylate,
Homosalate,
Butyl Methoxy Dibenzoylmethane,
Octocrylene,
Phenylbenzimidazole Sulfonic Acid,
Benzophenone-3,
Benzophenone-4,
Benzophenone-5,
n-Hexyl 2-(4-diethylamino-2-hydroxybenzoyl)benzoate,
4-Methylbenzylidene Camphor,
Terephthalylidene Dicamphor Sulfonic Acid,
Disodium Phenyl Dibenzimidazole Tetrasulfonate,
Methylene Bis-Benzotriazolyl Tetramethylbutylphenol,
Bis-Ethylhexyloxyphenyl Methoxyphenyl Triazine,
Ethylhexyl Triazone,
Diethylhexyl Butamido Triazone,
2,4,6-Tris(dineopentyl 4'-aminobenzalmalonate)-s-triazine,
2,4,6-Tris(diisobutyl 4'-aminobenzalmalonate)-s-triazine,
2,4-bis(n-butyl 4'-aminobenzoate)-6-(aminopropyltrisiloxane)-s-triazine,
2,4-Bis(dineopentyl 4'-aminobenzalmalonate)-6-(n-butyl 4'-aminobenzoate)-s-triazine,
2,4-Bis(n-butyl 4'-aminobenzalmalonate)-6-[(3-{1,3,3,3-tetramethyl-1-[(trimethylsilyl)oxy]disiloxanyl}propyl)amino]-s-triazine,
2,4,6-Tris(diphenyl)triazine,
2,4,6-Tris(terphenyl)triazine,
Drometrizole trisiloxane,
Polysilicone-15,
1,1-Dicarboxy(2,2'-dimethylpropyl)-4,4-diphenylbutadiene,
2,4-Bis[4[5-(1,1-dimethylpropyl)benzoxazol-2-yl]phenylimino]-6-[(2-ethylhexyl)imino-1,3,5-triazine,
and mixtures thereof.

The particularly preferred organic screening agents are chosen from:
Ethylhexyl salicylate,
Homosalate,
Butylmethoxydibenzoylmethane,
Octocrylene,
n-Hexyl 2-(4-diethylamino-2-hydroxybenzoyl)benzoate,
Terephthalylidene Dicamphor Sulfonic Acid,
Bis(ethylhexyloxyphenol)methoxyphenyltriazine,
Ethylhexyl Triazone,
Diethylhexyl Butamido Triazone,
2,4-Bis(n-butyl 4'-aminobenzalmalonate)-6-[(3-{1,3,3,3-tetramethyl-1-[(trimethylsilyl)oxy]disiloxanyl}propyl)amino]-s-triazine,
Drometrizole Trisiloxane,
and mixtures thereof.

The mineral UV-screening agents used in accordance with the present invention are metal oxide pigments. More preferentially, the mineral UV-screening agents are metal oxide particles with a mean elementary particle size of less than or equal to 0.5 µm, more preferentially between 0.005 and 0.5 µm, even more preferentially between 0.01 and 0.2 µm, better still between 0.01 and 0.1 µm and more particularly between 0.015 and 0.05 µm.

They may be selected in particular from titanium oxide, zinc oxide, iron oxide, zirconium oxide and cerium oxide, or mixtures thereof.

Such coated or uncoated metal oxide pigments are described in particular in patent application EP-A-0 518 773. Commercial pigments that may be mentioned include the products sold by the companies Sachtleben Pigments, Tayca, Merck and Degussa.

The metal oxide pigments may be coated or uncoated.

The coated pigments are pigments that have undergone one or more surface treatments of chemical, electronic, mechanochemical and/or mechanical nature with compounds such as amino acids, beeswax, fatty acids, fatty alcohols, anionic surfactants, lecithins, sodium, potassium, zinc, iron or aluminium salts of fatty acids, metal alkoxides (of titanium or aluminium), polyethylene, silicones, proteins (collagen, elastin), alkanolamines, silicon oxides, metal oxides or sodium hexametaphosphate.

The coated pigments are more particularly titanium oxides that have been coated:
- with silica, such as the product Sunveil® from the company Ikeda,
- with silica and iron oxide, such as the product Sunveil F® from the company Ikeda,
- with silica and alumina, such as the products Microtitanium Dioxide MT 500 SA® and Microtitanium Dioxide MT 100 SA from the company Tayca and Tioveil from the company Tioxide,
- with alumina, such as the products Tipaque TTO-55 (B)® and Tipaque TTO-55 (A)® from the company Ishihara and UVT 14/4 from the company Sachtleben Pigments,
- with alumina and aluminium stearate, such as the products Microtitanium Dioxide MT 100 T®, MT 100 TX®, MT 100 Z® and MT-01® from the company Tayca, the products Solaveil CT-10 W® and Solaveil CT 100® from the company Uniqema and the product Eusolex T-AVO® from the company Merck,
- with silica, alumina and alginic acid, such as the product MT-100 AQ® from the company Tayca,
- with alumina and aluminium laurate, such as the product Microtitanium Dioxide MT 100 S® from the company Tayca,
- with iron oxide and iron stearate, such as the product Microtitanium Dioxide MT 100 F® from the company Tayca,
- with zinc oxide and zinc stearate, such as the product BR 351® from the company Tayca,
- with silica and alumina and treated with a silicone, such as the products Microtitanium Dioxide MT 600 SAS®, Microtitanium Dioxide MT 500 SAS® or Microtitanium Dioxide MT 100 SAS® from the company Tayca,
- with silica, alumina and aluminium stearate and treated with a silicone, such as the product STT-30-DS® from the company Titan Kogyo,
- with silica and treated with a silicone, such as the product UV-Titan X 195® from the company Sachtleben Pigments,
- with alumina and treated with a silicone, such as the products Tipaque TTO-55 (S)® from the company Ishihara or UV Titan M 262® from the company Sachtleben Pigments,
- with triethanolamine, such as the product STT-65-S from the company Titan Kogyo,
- with stearic acid, such as the product Tipaque TTO-55 (C)® from the company Ishihara,
- with sodium hexametaphosphate, such as the product Microtitanium Dioxide MT 150 W® from the company Tayca,
- $TiO_2$ treated with octyltrimethylsilane, sold under the trade name T 805® by the company Degussa Silices,
- $TiO_2$ treated with a polydimethylsiloxane, sold under the trade name 70250 Cardre UF TiO2SI3® by the company Cardre,
- anatase/rutile $TiO_2$ treated with a polydimethylhydrogenosiloxane, sold under the trade name Microtitanium Dioxide USP Grade Hydrophobic® by the company Color Techniques.

Mention may also be made of $TiO_2$ pigments doped with at least one transition metal such as iron, zinc or manganese and more particularly manganese.

Preferably, the said doped pigments are in the form of an oily dispersion. The oil present in the oily dispersion is preferably chosen from triglycerides including those of capric/caprylic acids. The oily dispersion of titanium oxide particles may also comprise one or more dispersants, for instance a sorbitan ester, for instance sorbitan isostearate, or a polyoxyalkylenated fatty acid ester of glycerol, for instance TRI-PPG3 myristyl ether citrate and polyglyceryl-3 polyricinoleate. Preferably, the oily dispersion of titanium oxide particles comprises at least one dispersant chosen from polyoxyalkylenated fatty acid esters of glycerol. Mention may be made more particularly of the oily dispersion of $TiO_2$ particles doped with manganese in capric/caprylic acid triglycerides in the presence of TRI-PPG-3 myristyl ether citrate and polyglyceryl-3 polyricinoleate and sorbitan isostearate having the INCI name: titanium dioxide (and) TRI-PPG-3 myristyl ether citrate (and) polyglyceryl-3 ricinoleate (and) sorbitan isostearate, for instance the product sold under the trade name Optisol TD500 by the company Croda.

The uncoated titanium oxide pigments are sold, for example, by the company Tayca under the trade names Microtitanium Dioxide MT 500 B or Microtitanium Dioxide MT 600 B®, by the company Degussa under the name P 25, by the company Wackher under the name Transparent titanium oxide PW®, by the company Miyoshi Kasei under the name UFTR®, by the company Tomen under the name ITS® and by the company Tioxide under the name Tioveil AQ.

The uncoated zinc oxide pigments are for example:
- those sold under the name Z-Cote by the company Sunsmart;
- those sold under the name Nanox® by the company Elementis;
- those sold under the name Nanogard WCD 2025® by the company Nanophase Technologies.

The coated zinc oxide pigments are for example:
- those sold under the name Zinc Oxide CS-50 by the company Toshibi (ZnO coated with polymethylhydrogenosiloxane);
- those sold under the name Nanogard Zinc Oxide FN® by the company Nanophase Technologies (as a 40% dispersion in Finsolv TN®, $C_{12}$-$C_{15}$ alkyl benzoate);
- those sold under the name Daitopersion Zn-30® and Daitopersion Zn-500 by the company Daito (dispersions in cyclopolymethylsiloxane/oxyethylenated polydimethylsiloxane, containing 30% or 50% of zinc oxides coated with silica and polymethylhydrogenosiloxane);
- those sold under the name NFD Ultrafine ZnO® by the company Daikin (ZnO coated with perfluoroalkyl phosphate and copolymer based on perfluoroalkylethyl as a dispersion in cyclopentasiloxane);
- those sold under the name SPD-Z1® by the company Shin-Etsu (ZnO coated with silicone-grafted acrylic polymer, dispersed in cyclodimethylsiloxane);
- those sold under the name Escalol Z100@ by the company ISP (alumina-treated ZnO dispersed in an ethylhexyl methoxycinnamate/PVP-hexadecene copolymer/methadone mixture);

those sold under the name Fuji ZnO-SMS-10® by the company Fuji Pigment (ZnO coated with silica and polymethylsilsesquioxane);

those sold under the name Nanox Gel TN® by the company Elementis (ZnO dispersed at a concentration of 55% in $C_{12}$-$C_{15}$ alkyl benzoate with hydroxystearic acid polycondensate).

The uncoated cerium oxide pigments may be, for example, those sold under the name Colloidal Cerium Oxide® by the company Rhône-Poulenc.

The uncoated iron oxide pigments are sold, for example, by the company Arnaud under the names Nanogard WCD 2002® (FE 45B®), Nanogard Iron FE 45 BL AQ, Nanogard FE 45R AQ® and Nanogard WCD 2006® (FE 45R®) or by the company Mitsubishi under the name TY-220®.

The coated iron oxide pigments are sold, for example, by the company Arnaud under the names Nanogard WCD 2008 (FE 45B FN)®, Nanogard WCD 2009® (FE 45B 556®), Nanogard FE 45 BL 345® and Nanogard FE 45 BL® or by the company BASF under the name Transparent Iron Oxide®.

Mention may also be made of mixtures of metal oxides, in particular of titanium dioxide and of cerium dioxide, including the equal-weight mixture of titanium dioxide and cerium dioxide coated with silica, sold by the company Ikeda under the name Sunveil A®, and also the mixture of titanium dioxide and zinc dioxide coated with alumina, silica and silicone, such as the product M 261® sold by the company Sachtleben Pigments, or coated with alumina, silica and glycerol, such as the product M 211® sold by the company Sachtleben Pigments.

According to the invention, coated or uncoated titanium oxide pigments are particularly preferred.

The additional UV-screening agents according to the invention are preferably present in the compositions according to the invention in a proportion ranging from 0.1% to 45% by weight and in particular from 5% to 30% by weight, relative to the total weight of the composition.

b) Other Additives

The aqueous compositions in accordance with the present invention may also comprise conventional cosmetic adjuvants chosen in particular from organic solvents, ionic or nonionic thickeners, softeners, humectants, opacifiers, stabilizers, emollients, silicones, antifoams, fragrances, preserving agents, anionic, cationic, nonionic, zwitterionic or amphoteric surfactants, active agents, fillers, polymers, propellants, acidifying or basifying agents, or any other ingredient commonly used in the cosmetic and/or dermatological field.

Among the organic solvents that may be mentioned are alcohols other than $C_1$-$C_4$ monoalkanols as defined above and in particular short-chain $C_2$-$C_8$ polyols, for instance glycerol, diols, for instance caprylylglycol, 1,2-pentanediol, propanediol, butanediol, glycols and glycol ethers, for instance ethylene glycol, propylene glycol, butylene glycol, dipropylene glycol or diethylene glycol.

Thickeners that may be mentioned include carboxyvinyl polymers such as the Carbopol® products (Carbomers) and the Pemulen products, for instance Pemulen TR1® and Pemulen TR2® (acrylate/$C_{10}$-$C_{30}$ alkyl acrylate copolymer); polyacrylamides, for instance the crosslinked copolymers sold under the names Sepigel 305® (CTFA name: polyacrylamide/$C_{13-14}$ isoparaffin/Laureth 7) or Simulgel 600 (CTFA name: acrylamide/sodium acryloyldimethyltaurate copolymer/isohexadecane/polysorbate 80) by the company SEPPIC; 2-acrylamido-2-methylpropanesulfonic acid polymers and copolymers, optionally crosslinked and/or neutralized, for instance poly(2-acrylamido-2-methylpropanesulfonic acid) sold by the company Hoechst under the trade name Hostacerin AMPS® (CTFA name: ammonium polyacryloyldimethyl taurate or Simulgel 800® sold by the company SEPPIC (CTFA name: sodium polyacryolyldimethyl taurate/polysorbate 80/sorbitan oleate); copolymers of 2-acrylamido-2-methylpropanesulfonic acid and of hydroxyethyl acrylate, for instance Simulgel NS® and Sepinov EMT 10® sold by the company SEPPIC; cellulose derivatives such as hydroxyethylcellulose; polysaccharides and especially gums such as xanthan gum; water-soluble or water-dispersible silicone derivatives, for instance acrylic silicones, polyether silicones and cationic silicones, and mixtures thereof.

Among the acidifying agents, examples that may be mentioned include mineral or organic acids, for instance hydrochloric acid, orthophosphoric acid, sulfuric acid, carboxylic acids, for instance acetic acid, tartaric acid, citric acid or lactic acid, and sulfonic acids.

Among the basifying agents, examples that may be mentioned include aqueous ammonia, alkali metal carbonates, alkanolamines such as monoethanolamine, diethanolamine and triethanolamine, and also derivatives thereof, sodium hydroxide and potassium hydroxide.

Preferably, the cosmetic composition comprises one or more basifying agents chosen from alkanolamines, in particular triethanolamine, and sodium hydroxide.

In the case of a direct emulsion, the pH of the composition in accordance with the invention is generally between 3 and 12 approximately, preferably between 5 and 11 approximately and even more particularly from 6 to 8.5.

Among the active agents for caring for keratin materials such as the skin, the lips, the scalp, the hair, the eyelashes or the nails, examples that may be mentioned include:

vitamins and derivatives or precursors thereof, alone or as mixtures;
antioxidants;
free-radical scavengers;
antipollution agents;
self-tanning agents;
antiglycation agents;
calmatives;
deodorants;
essential oils;
NO-synthase inhibitors;
agents for stimulating the synthesis of dermal or epidermal macromolecules and/or which prevent their decomposition;
agents for stimulating the proliferation of fibroblasts;
agents for stimulating the proliferation of keratinocytes;
muscle relaxants;
refreshing agents;
tensioning agents;
mattifying agents;
depigmenting agents;
propigmenting agents;
keratolytic agents;
desquamating agents;
moisturizers;
antiinflammatory agents;
antimicrobial agents;
slimming agents;
agents acting on the energy metabolism of cells;
insect repellents;
substance P or CGRP antagonists;
hair-loss counteractants;
antiwrinkle agents;
antiageing agents.

A person skilled in the art will select the said active principle(s) according to the effect desired on the skin, the hair, the eyelashes, the eyebrows or the nails.

Needless to say, a person skilled in the art will take care to select the abovementioned optional additional compound(s) and/or the amounts thereof such that the advantageous properties intrinsically associated with the compositions in accordance with the invention are not, or are not substantially, adversely affected by the envisaged addition(s).

Galenical Forms

The compositions according to the invention may be prepared according to the techniques that are well known to those skilled in the art. They may be, in particular, in the form of a simple or complex emulsion (O/W, W/O, O/W/O or W/O/W) such as a cream, a milk or of a gel cream.

They may also be in anhydrous form, for instance in the form of an oil. The term "anhydrous composition" means a composition containing less than 1% by weight of water, or even less than 0.5% of water, and especially free of water, the water not being added during the preparation of the composition, but corresponding to the residual water provided by the mixed ingredients. They may optionally be packaged as aerosols and may be in the form of a mousse or a spray.

In the case of compositions in the form of oil-in-water or water-in-oil emulsions, the emulsification processes that may be used are of the paddle or impeller, rotor-stator and HPH type.

In order to obtain stable emulsions with a low content of polymer (oil/polymer ratio>25), it is possible to prepare the dispersion in concentrated phase and then to dilute the dispersion with the remainder of the aqueous phase.

It is also possible, by means of an HPH (between 50 and 800 bar), to obtain stable dispersions with drop sizes that may be as low as 100 nm.

The emulsions generally comprise at least one emulsifier chosen from amphoteric, anionic, cationic and nonionic emulsifiers, used alone or as a mixture. The emulsifiers are appropriately chosen according to the emulsion to be obtained (W/O or O/W).

Examples of W/O emulsifying surfactants that may be mentioned include alkyl esters or ethers of sorbitan, of glycerol, of polyol or of sugars; silicone surfactants, for instance dimethicone copolyols, such as the mixture of cyclomethicone and of dimethicone copolyol, sold under the name DC 5225 C® by the company Dow Corning, and alkyldimethicone copolyols such as laurylmethicone copolyol sold under the name Dow Corning 5200 Formulation Aid by the company Dow Corning; cetyldimethicone copolyol, such as the product sold under the name Abil EM 90R® by the company Goldschmidt, and the mixture of cetyldimethicone copolyol, of polyglyceryl isostearate (4 mol) and of hexyl laurate, sold under the name Abil WE O9® by the company Goldschmidt. One or more coemulsifiers may also be added thereto, which may be chosen advantageously from the group consisting of polyol alkyl esters.

Mention may also be made of non-silicone emulsifying surfactants, in particular alkyl esters or ethers of sorbitan, of glycerol, of polyol or of sugars.

Polyol alkyl esters that may especially be mentioned include polyethylene glycol esters, for instance PEG-30 dipolyhydroxystearate, such as the product sold under the name Arlacel P135® by the company ICI.

Examples of glycerol and/or sorbitan esters that may be mentioned include polyglyceryl isostearate, such as the product sold under the name Isolan GI 34® by the company Goldschmidt; sorbitan isostearate, such as the product sold under the name Arlacel 987® by the company ICI; sorbitan glyceryl isostearate, such as the product sold under the name Arlacel 986® by the company ICI, and mixtures thereof.

For the O/W emulsions, examples of nonionic emulsifying surfactants that may be mentioned include polyoxyalkylenated (more particularly polyoxyethylenated and/or polyoxypropylenated) esters of fatty acids and of glycerol; oxyalkylenated esters of fatty acids and of sorbitan; polyoxyalkylenated (in particular polyoxyethylenated and/or polyoxypropylenated) esters of fatty acids, optionally in combination with an ester of fatty acid and of glycerol, such as the PEG-100 stearate/glyceryl stearate mixture sold, for example, by ICI under the name Arlacel 165; oxyalkylenated (oxyethylenated and/or oxypropylenated) ethers of fatty alcohols; esters of sugars, such as sucrose stearate; or ethers of fatty alcohol and of sugar, in particular alkyl polyglucosides (APGs), such as decyl glucoside and lauryl glucoside, sold, for example, by the company Henkel under the respective names Plantaren 2000® and Plantaren 1200®, cetearyl glucoside, optionally as a mixture with cetearyl alcohol, sold, for example, under the name Montanov 68® by the company SEPPIC, under the name Tegocare CG90® by the company Goldschmidt and under the name Emulgade KE3302® by the company Henkel, and arachidyl glucoside, for example in the form of the mixture of arachidyl and behenyl alcohols and of arachidyl glucoside sold under the name Montanov 202® by the company SEPPIC. According to a particular embodiment of the invention, the mixture of the alkylpolyglucoside as defined above with the corresponding fatty alcohol may be in the form of a self-emulsifying composition, for example as described in document WO-A-92/06778.

When it is an emulsion, the aqueous phase of this emulsion may comprise a nonionic vesicular dispersion prepared according to known processes (Bangham, Standish and Watkins, J. Mol. Biol., 13, 238 (1965), FR 2 315 991 and FR 2 416 008)

The compositions according to the invention find their application in a large number of treatments, especially cosmetic treatments, of the skin, the lips and the hair, including the scalp, especially for protecting and/or caring for the skin, the lips and/or the hair, and/or for making up the skin and/or the lips.

Another subject of the present invention consists of the use of the compositions according to the invention as defined above for the manufacture of products for the cosmetic treatment of the skin, the lips, the nails, the hair, the eyelashes, the eyebrows and/or the scalp, especially care products, antisun products and makeup products.

The cosmetic compositions according to the invention may be used, for example, as makeup products.

Another subject of the present invention consists of a non-therapeutic cosmetic process for caring for and/or making up a keratin material, which consists in applying, to the surface of the said keratin material, at least one composition according to the invention as defined above.

The cosmetic compositions according to the invention may be used, for example, as care products and/or antisun protection products for the face and/or the body, of liquid to semi-liquid consistency, such as milks, more or less smooth creams, gel creams, and pastes. They may optionally be packaged in aerosol form and may be in the form of a mousse or a spray.

The compositions according to the invention in the form of vaporizable fluid lotions in accordance with the invention are applied to the skin or the hair in the form of fine particles by means of pressurization devices. The devices in accordance with the invention are well known to those skilled in the art and comprise non-aerosol pumps or "atomizers", aerosol containers comprising a propellant and aerosol pumps using compressed air as propellant. These devices are described in patents U.S. Pat. No. 4,077,441 and U.S. Pat. No. 4,850,517.

The compositions packaged as an aerosol in accordance with the invention generally comprise conventional propellants, such as, for example, hydrofluoro compounds, dichlorodifluoromethane, difluoroethane, dimethyl ether, isobutane, n-butane, propane or trichlorofluoromethane. They are preferably present in amounts ranging from 15% to 50% by weight relative to the total weight of the composition.

ASSEMBLY

According to another aspect, the invention also relates to a cosmetic assembly comprising:
i) a container delimiting one or more compartment(s), the said container being closed by a closing member and optionally not being leaktight; and
ii) a makeup and/or care composition in accordance with the invention placed inside the said compartment(s).

The container may be, for example, in the form of a jar or a box.

The closing member may be in the form of a lid comprising a cap mounted so as to be able to move by translation or by pivoting relative to the container housing the said makeup and/or care composition(s).

The examples that follow serve to illustrate the invention without, however, being limiting in nature. In these examples, the amounts of the composition ingredients are given as % by weight, relative to the total weight of the composition.

Example A1: Preparation of Compound (14)

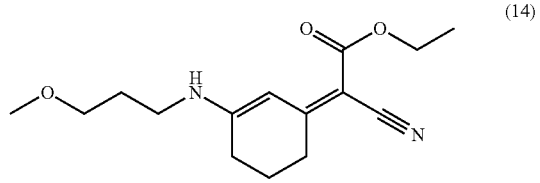 [SMILES: CCOC(=O)/C(C#N)=C1\C=C(NCCCOC)CCC1]

(14)

122.23 g of 3-[(3-methoxypropyl)amino]-2-cyclohexen-1-one were alkylated with dimethyl sulfate or alternatively with diethyl sulfate and treated with 75.45 g of ethyl cyanoacetate in approximately equimolar proportions in the presence of a base and optionally of a solvent.

The following base/solvent combinations are used:

| Example | Base | Solvent |
| --- | --- | --- |
| Example A1.1 | DBU (1,8-diazabi-cyclo[5.4.0]undec-7-ene) | dimethylacetamide |
| Example A1.2 | triethylamine | isopropanol |
| Example A1.3 | 3-methoxypropylamine | isopropanol |
| Example A1.4 | 3-methoxypropylamine | tert-amyl alcohol |
| Example A1.5 | 3-methoxypropylamine | toluene |
| Example A1.6 | 3-methoxypropylamine | dimethylformamide |
| Example A1.7 | 3-methoxypropylamine | no solvent |
| Example A1.8 | N-morpholine | isopropanol |

The completion of the alkylation reaction may be monitored, for example, via methods such as TLC, GC or HPLC.

162.30 g of compound (14) are obtained in the form of a brown oil.

After crystallization, the product is obtained in the form of yellowish crystals.

Melting point: 92.7° C.

Example A2: Preparation of Compound (15)

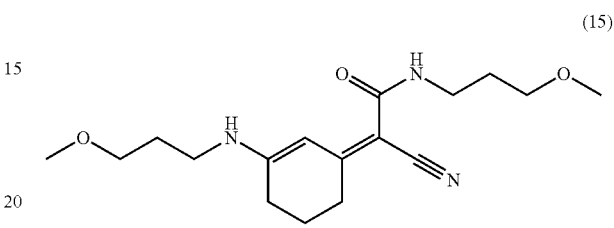

(15)

101.00 g of 3-[(3-methoxypropyl)amino]-2-cyclohexen-1-one are alkylated with dimethyl sulfate or alternatively with diethyl sulfate and treated with 86.00 g of 2-cyano-N-(3-methoxypropyl)acetamide in approximately equimolar proportions in the presence of a base and optionally of a solvent.

The following base/solvent combinations are used:

| Example | Base | Solvent |
| --- | --- | --- |
| Example A2.1 | DBU (1,8-diazabi-cyclo[5.4.0]undec-7-ene) | dimethylacetamide |
| Example A2.2 | triethylamine | isopropanol |
| Example A2.3 | 3-methoxypropylamine | isopropanol |
| Example A2.4 | 3-methoxypropylamine | tert-amyl alcohol |
| Example A2.5 | 3-methoxypropylamine | toluene |
| Example A2.6 | 3-methoxypropylamine | dimethylformamide |
| Example A2.7 | 3-methoxypropylamine | no solvent |

The crude product (15) is obtained in the form of a dark brown oil.

After chromatography on a column of silica gel (eluent: 99/1 toluene/methanol), 81.8 g of product are obtained in the form of yellowish crystals.

Melting point: 84.7-85.3° C.

Example A3: Preparation of Compound (27)

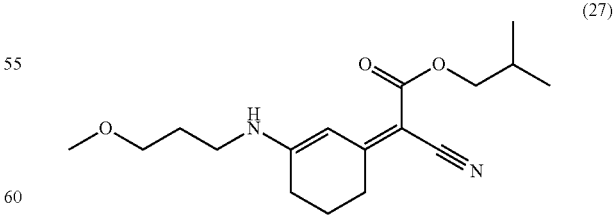

(27)

13.09 g of 3-[(3-methoxypropyl)amino]-2-cyclohexen-1-one are alkylated with dimethyl sulfate or alternatively with diethyl sulfate and treated with 10.12 g of isobutyl cyanoacetate in approximately equimolar proportions in the presence of a base and optionally of a solvent.

The following base/solvent combinations are used:

| Example | Base | Solvent |
| --- | --- | --- |
| Example A3.1 | DBU (1,8-diazabi-cyclo[5.4.0]undec-7-ene) | dimethylacetamide |
| Example A3.2 | triethylamine | isopropanol |
| Example A3.3 | 3-methoxypropylamine | isopropanol |
| Example A3.4 | N-methylmorpholine | tert-amyl alcohol |
| Example A3.5 | 3-methoxypropylamine | toluene |
| Example A3.6 | 3-methoxypropylamine | dimethylformamide |
| Example A3.7 | 3-methoxypropylamine | no solvent |

15.97 g of the crude product (27) are obtained in the form of a dark brown oil.

After chromatography on a column of silica gel (eluent: toluene/acetone), 13.46 g of product are obtained in the form of yellowish crystals.

Melting point: 96.3° C.

Example A4: Preparation of Compound (25)

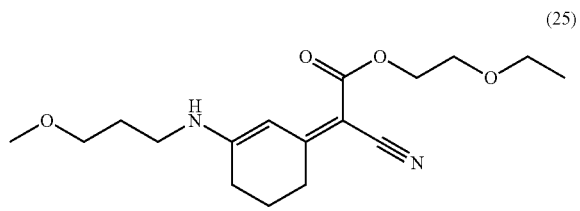 [SMILES: CCOCCOC(=O)/C(C#N)=C1\C=C(NCCCOC)CCC1]

(25)

148.4 g of 3-[(3-methoxypropyl)amino]-2-cyclohexen-1-one are alkylated with dimethyl sulfate or alternatively with diethyl sulfate and treated with 130.00 g of 2-ethoxyethyl cyanoacetate in the presence of a base and a solvent.

The following base/solvent combinations are used:

| Example | Base | Solvent |
| --- | --- | --- |
| Example A4.1 | DBU (1,8-diazabi-cyclo[5.4.0]undec-7-ene) | dimethylacetamide |
| Example A4.2 | triethylamine | isopropanol |
| Example A4.3 | 3-methoxypropylamine | isopropanol |
| Example A4.4 | N-methylmorpholine | tert-amyl alcohol |
| Example A4.5 | 3-methoxypropylamine | toluene |
| Example A4.6 | 3-methoxypropylamine | dimethylformamide |
| Example A4.7 | 3-methoxypropylamine | no solvent |

FORMULATION EXAMPLES

Examples 1 to 3: Oily Solutions

The following oily solutions were prepared according to the processes described below.

| Ingredients | Formulation 1 (invention) | Formulation 2 (invention) | Formulation 3 (outside the invention) |
| --- | --- | --- | --- |
| Compound (25) | 10 | 20 | 10 |
| N,N-Dimethylcapramide | 90 | 80 | — |
| Isopropyl lauroyl sarcosinate (Eldew SL205 ® from Ajinomoto) | — | — | 90 |

| Ingredients | Formulation 1 (invention) | Formulation 2 (invention) | Formulation 3 (outside the invention) |
| --- | --- | --- | --- |
| Solubility at $t_0$ | soluble | soluble | soluble |
| solubility at $t_{1\,wk}$ | soluble | soluble | soluble |
| solubility at $t_{2\,wks}$ | soluble | soluble | insoluble |
| solubility at $t_{2\,M}$ | soluble | soluble | insoluble |

Oil Preparation Method:

The oily solutions described in the examples are prepared in the following manner: the merocyanine and the oil are successively introduced into a container before being stirred using a magnetic stirrer and being heated at 90° C. for between 10 minutes and 1 hour, until the merocyanine has dissolved.

Solubility Evaluation Protocol

The solubility of the merocyanine in the oily solutions is evaluated macroscopically and microscopically. It is estimated that the merocyanine is soluble if, at room temperature, the solution appears clear and translucent to the eye, and if it does not have any visible crystals under a microscope in white or polarized light (×20 to ×40 objective lens). The solubility is evaluated at room temperature, on the day of preparation of the solution ("solubility at $t_0$"), 1 week later ("solubility at $t_{1\,wk}$"), 2 weeks later ("solubility at $t_{2\,wks}$") and 2 months after preparation ("solubility at $t_{2M}$"). During this interval, the solutions are stored at room temperature.

Examples 4 and 5: Emulsions

| Phase | Ingredients | Formulation 4 (invention) | Formulation 5 (outside the invention) |
| --- | --- | --- | --- |
| A | Water | qs 100 | qs 100 |
| | Glycerol | 5 | 5 |
| | Triethanolamine | 0.45 | 0.45 |
| | Disodium EDTA | 0.1 | 0.1 |
| | Ammonium acryloyldimethyltaurate/steareth-8 methacrylate copolymer (aqueous solution at 92% by weight - Aristoflex SNC ® from Clariant) | 0.5 | 0.5 |
| B | Butylmethoxydibenzoylmethane (Parsol 1789 ®) | 2 | 2 |
| | Compound 25 | 1 | 1 |
| | N,N-Dimethylcapramide (Hallcomid ® M-10 by the company Stepan) | 15 | — |
| | Isopropyl lauroyl sarcosinate (Eldew SL 205 ®) | — | 30 |
| | Stearyl alcohol | 1 | 1 |
| | Glyceryl isostearate | 0.5 | 0.5 |
| | Preserving agent | 1 | 1 |
| C | Isohexadecane | 1 | 1 |
| | Xanthan gum | 0.2 | 0.2 |
| | Ammonium polyacryldimethyltauramide (Hostacerin AMPS ®) | 0.4 | 0.4 |
| Microscopic observations at $t_{2\,M}$, 4° C. | | Absence of recrystallization | Recrystallization |

Method for Preparing the Emulsions:

The aqueous phase A and oily phase B were prepared by mixing the starting materials with mechanical stirring at 80° C. Once the oily solution B and aqueous solution A were macroscopically homogeneous, the emulsion was prepared by introducing phase B into phase A, stirred using a rotor-stator homogenizer at a stirring speed of 4500 rpm for 20 minutes. Phase C was then added, with continued stirring. The emulsion was finally cooled to room temperature. The final emulsion is characterized by drops between 1 µm and 20 µm in size.

Protocol for Evaluating the Solubility Maintenance in Formulation

The maintenance of the solubility of the merocyanine in the emulsions is evaluated by observing the emulsions under polarized light with a ×20 objective lens. The solubility is considered to be maintained if no crystals responding to the polarized light are detected after 2 months of storage of the formulation at 4° C.

These results show that the amides of the invention make it possible to maintain the solubility of the merocyanine for much longer than a reference amide, both in oily solution and in emulsion. They also make it possible to keep soluble at $t_{2M}$ a larger amount of merocyanine of the invention.

The invention claimed is:

1. A cosmetic or dermatological composition comprising, in a physiologically acceptable support comprising, in a physiologically acceptable medium:
   a) at least one of the following merocyanines present in a concentration ranging from 0.1% to 10% by weight relative to the total weight of the composition, the compound 2-ethoxyethyl (2Z)-cyano{3-[(3-methoxypropyl)amino]cyclohex-2-en-1-ylidene}ethanoate (25) in its E/Z geometrical configuration having the following structure:

and/or the E/E form having the following structure:

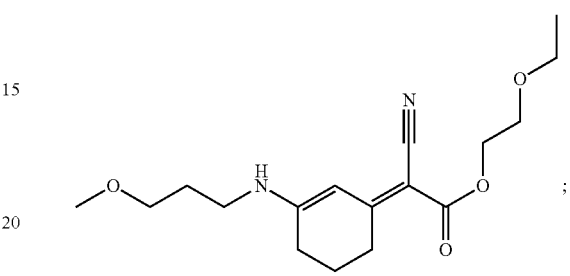

and
   b) at least one oily phase comprising at least one amide compound present in a concentration ranging from 0.1% to 50% by weight relative to the total weight of the cosmetic or dermatological composition and being selected from the group consisting of N,N-dimethylcapramide, N,N-dimethylcaprylamide or mixtures thereof.

2. A non-therapeutic cosmetic process for caring for and/or making up a keratin material, comprising the application, to the surface of the said keratin material, of at least one cosmetic or dermatological composition as defined in claim 1.

* * * * *